(12) United States Patent
Yong et al.

(10) Patent No.: US 6,620,844 B2
(45) Date of Patent: *Sep. 16, 2003

(54) METHOD FOR REDUCING BLOOD INSULIN LEVELS BY REDUCING IN VIVO CATHEPSIN L ACTIVITY

(75) Inventors: Hamilton H. Yong, Castro Valley, CA (US); Jingming Chen, Fremont, CA (US); Guo-ping Shi, Palo Alto, CA (US)

(73) Assignee: NewMillennium Pharmaceutical, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/784,642

(22) Filed: Feb. 14, 2001

(65) Prior Publication Data

US 2003/0054984 A1 Mar. 20, 2003

Related U.S. Application Data

(63) Continuation of application No. 09/784,646, filed on Feb. 14, 2001, and a continuation of application No. 09/784,641, filed on Feb. 14, 2001.

(51) Int. Cl.[7] .................. A61K 31/335; A61K 31/47; A61K 31/445; A61K 31/495

(52) U.S. Cl. .................. 514/475; 514/311; 514/326; 514/336; 514/252; 514/866

(58) Field of Search ............... 514/475, 336, 514/311.1, 394, 252, 326, 866

(56) References Cited

U.S. PATENT DOCUMENTS 5,883,121 A * 3/1999 Yamashita et al. .......... 514/475
6,110,967 A * 8/2000 Asao et al. .................. 514/475

FOREIGN PATENT DOCUMENTS

WO    WO 00/34781    7/1999

OTHER PUBLICATIONS

Desautels, M., et. al., "Role of acid proteases in brown adipose tissue atrophy caused by fasting in mice", Biochem. Cell Biol., vol. 68, pp. 441–447 (1990).

Gunderson, Kevin L., et al., "Mutation Detection by Ligation to Complete η–mer DNA Arrays", Gnome Research, 8:1142–1153 (1998).

Katunuma, N., et al., "Structure based development of novel specific inhibitors for cathespin L and cathespin S in vitro and in vivo", FEBS Letters, 458:pp. 6–10 (1999).

* cited by examiner

*Primary Examiner*—Kevin E. Weddington
(74) *Attorney, Agent, or Firm*—Shirley Chen; Wilson Sonsini Goodrich & Rosati

(57) ABSTRACT

Methods and compositions are provided for modulating blood insulin levels of animals by targeting the gene and gene products of cathepsins, particularly cathepsins L, K, and S, and especially cathepsin L. The method comprises: administering to the animal an agent that reduces an in vivo level of cathepsin L activity such that the blood insulin level of the animal is reduced. The method can be used to treat hyperinsulinmia and related diseases such as insulin resistance, type II diabetes, and hyperglycermia.

22 Claims, 11 Drawing Sheets

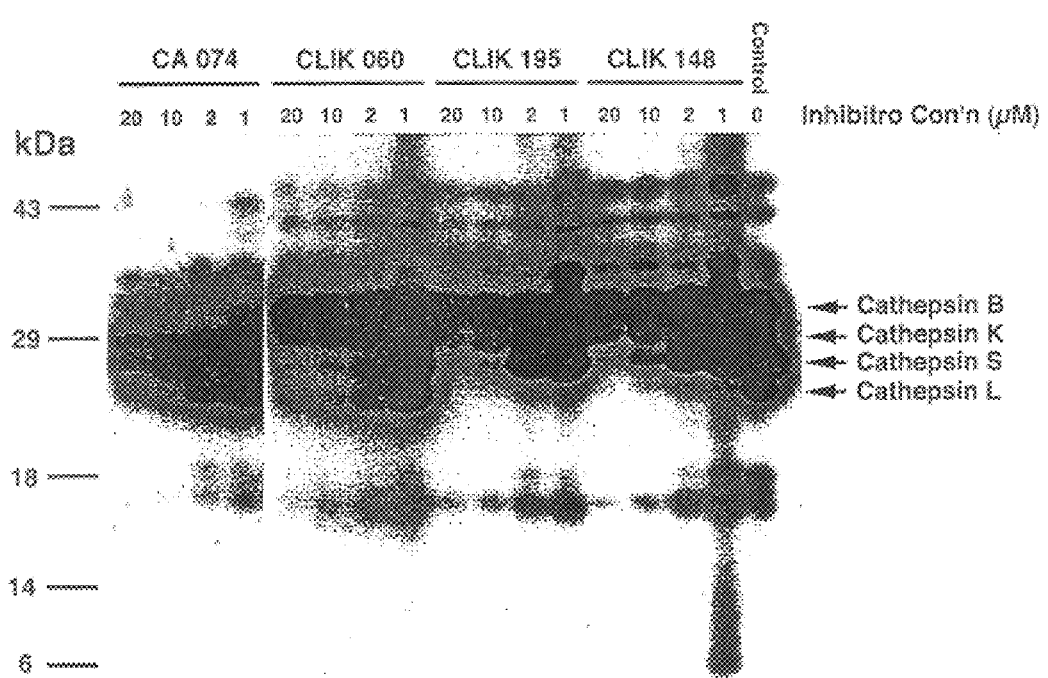
Fig 1. Cysteine protease inhibition profiles in mouse peritoneal macrophages.

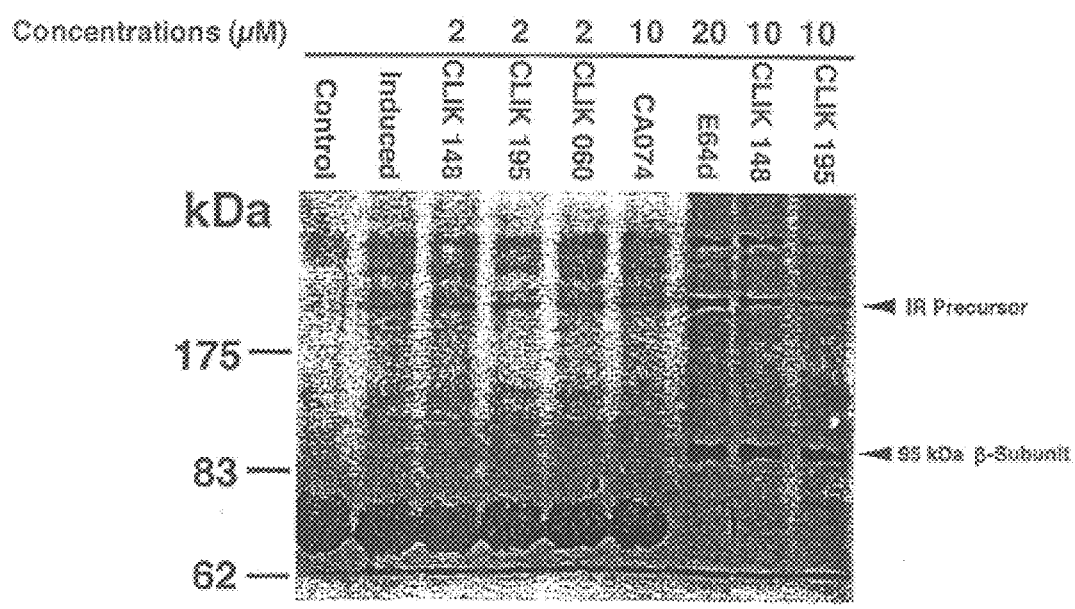
Fig 2. Inhibition of cathepsin L resulted in accumulation of 95 kDa insulin receptor beta subunit and its precursor.

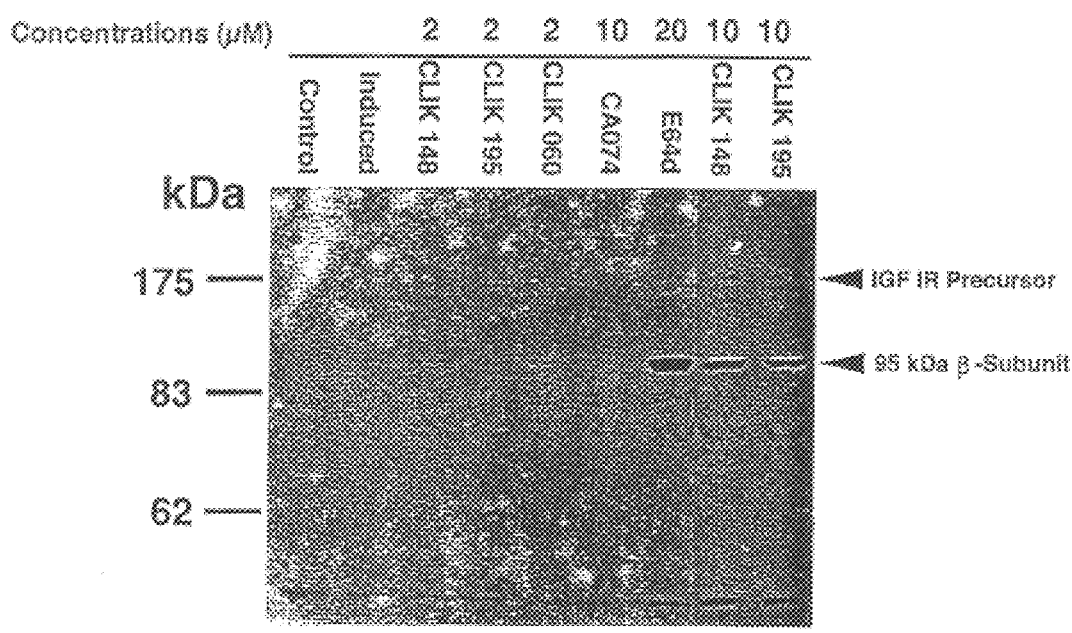
Fig 3. Inhibition of human cathepsin L resulted in accumulation of 95 kDa insulin receptor like protein beta subunit and its precursor.

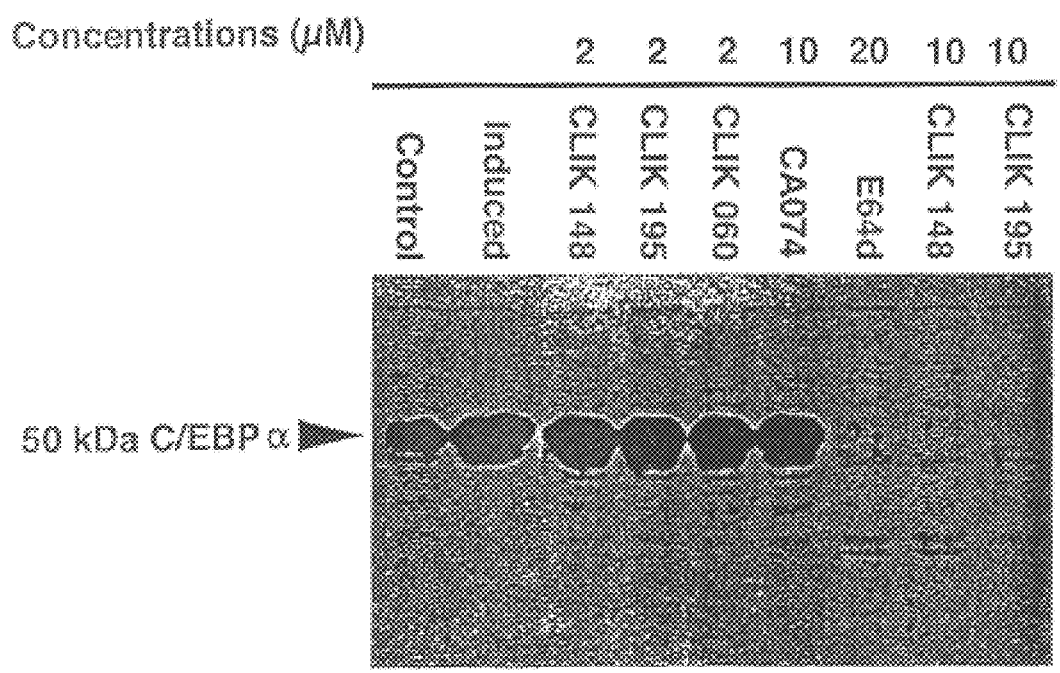
Fig. 4 Inhibition of cathepsin L blocked the expression of CCAAT/enhancer-binding protein alpha.

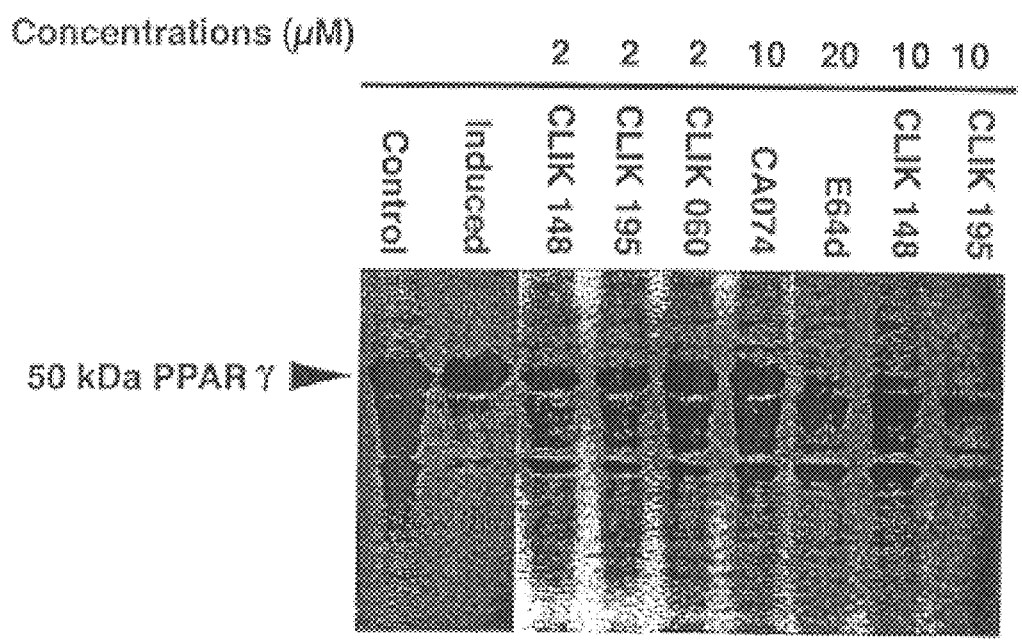
Fig. 5. Inhibition of cathepsin L blocked the expression of perxisome proliferator activated receptor gamma.

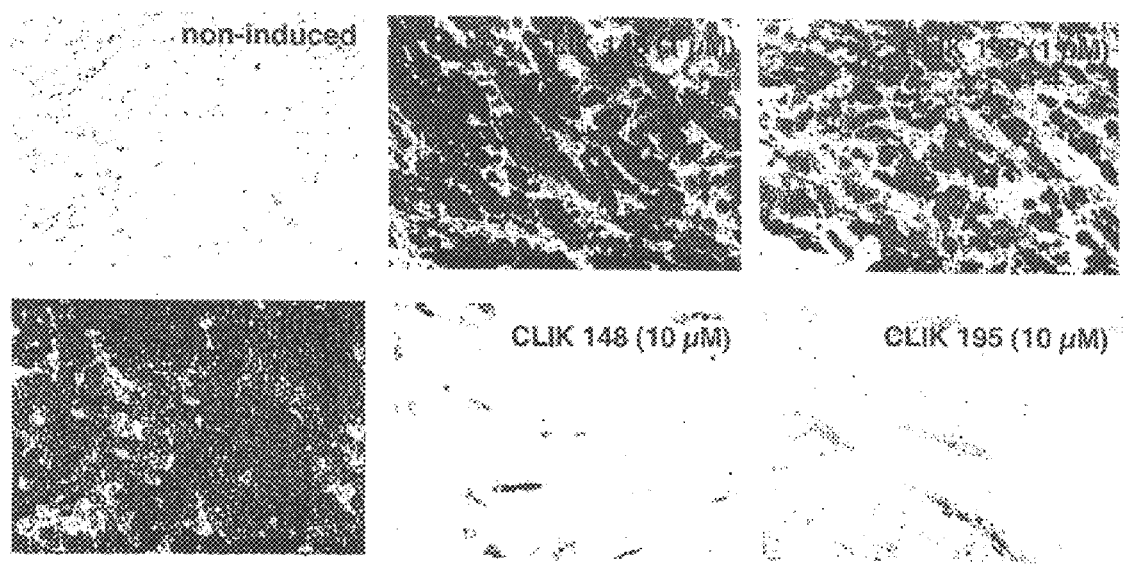
Fig 6. Human preadipocyte adipogenesis was completely blocked by synthetic cathepsin L inhibitors.

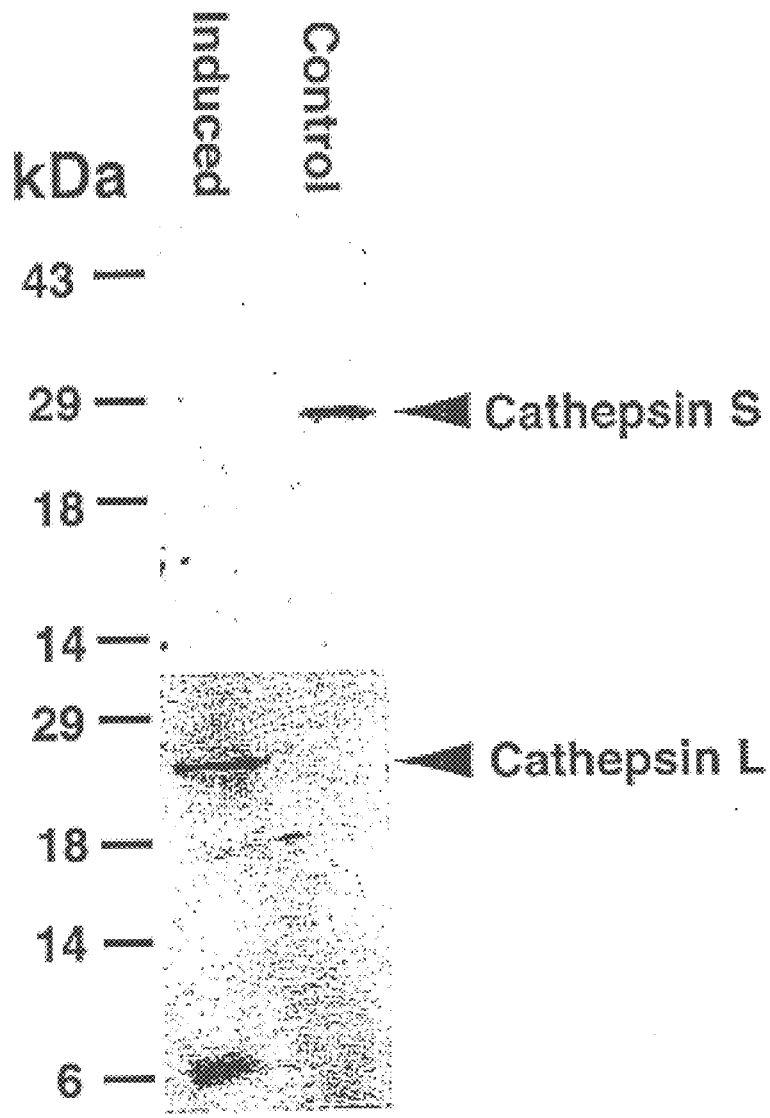
Fig 7. Decreased cathepsin S and increased cathepsin L expression in differentiated human adipocytes.

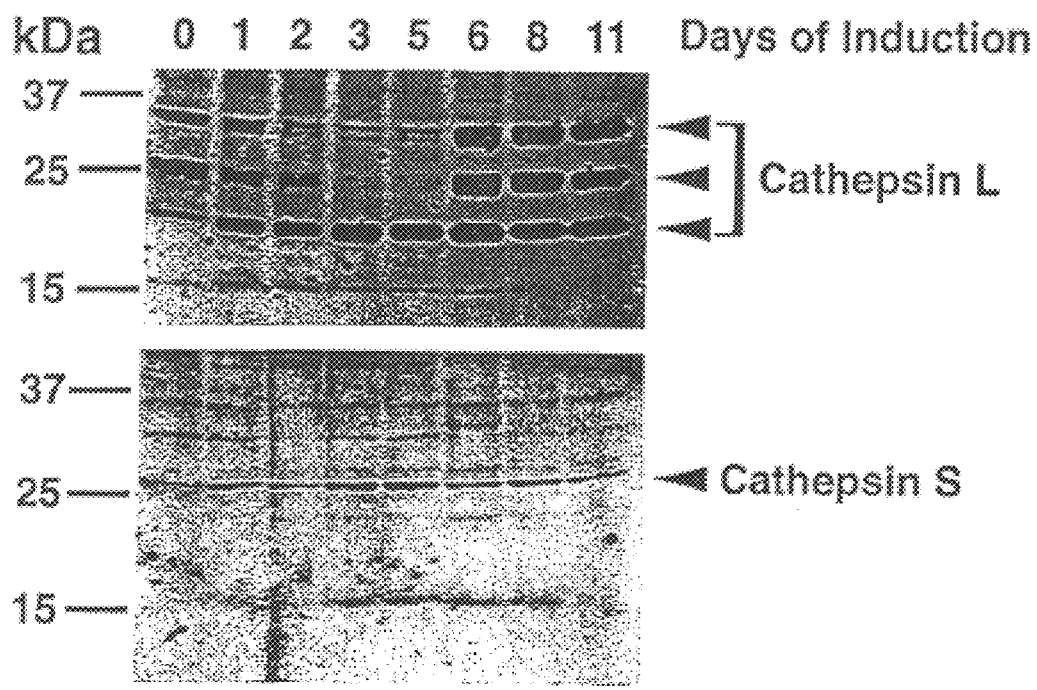
Fig 8. Cathepsins L and S expression during mouse 3T3-L1 preadipocyte differentiation.

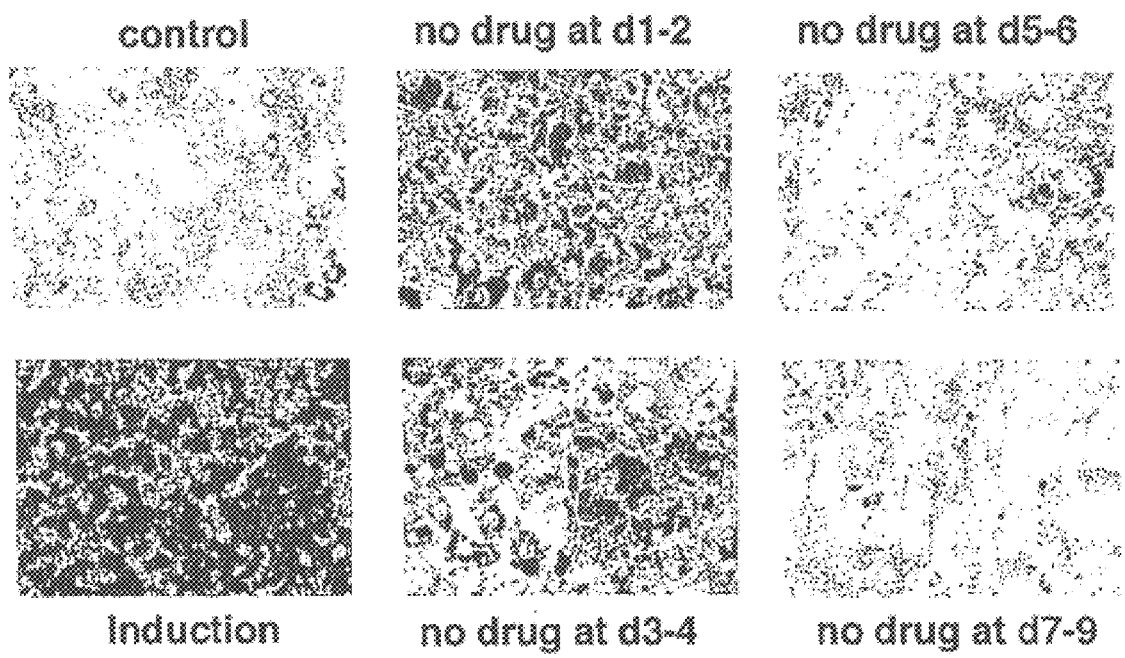
Fig 9. Effect of cathepsin L inhibitor during mouse 3T3-L1 preadipocyte differentiation.

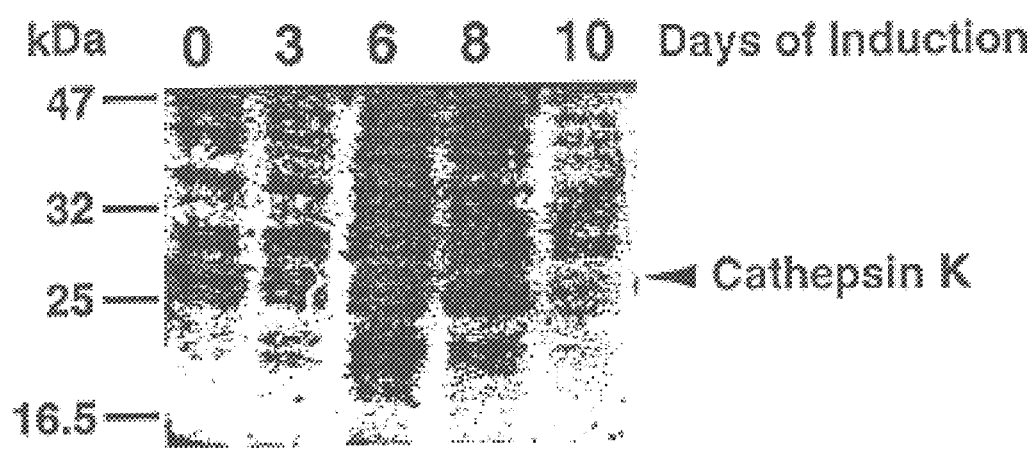
Fig 10. Decreased expression of cathepsin K during mouse 3T3-L1 differentiation.

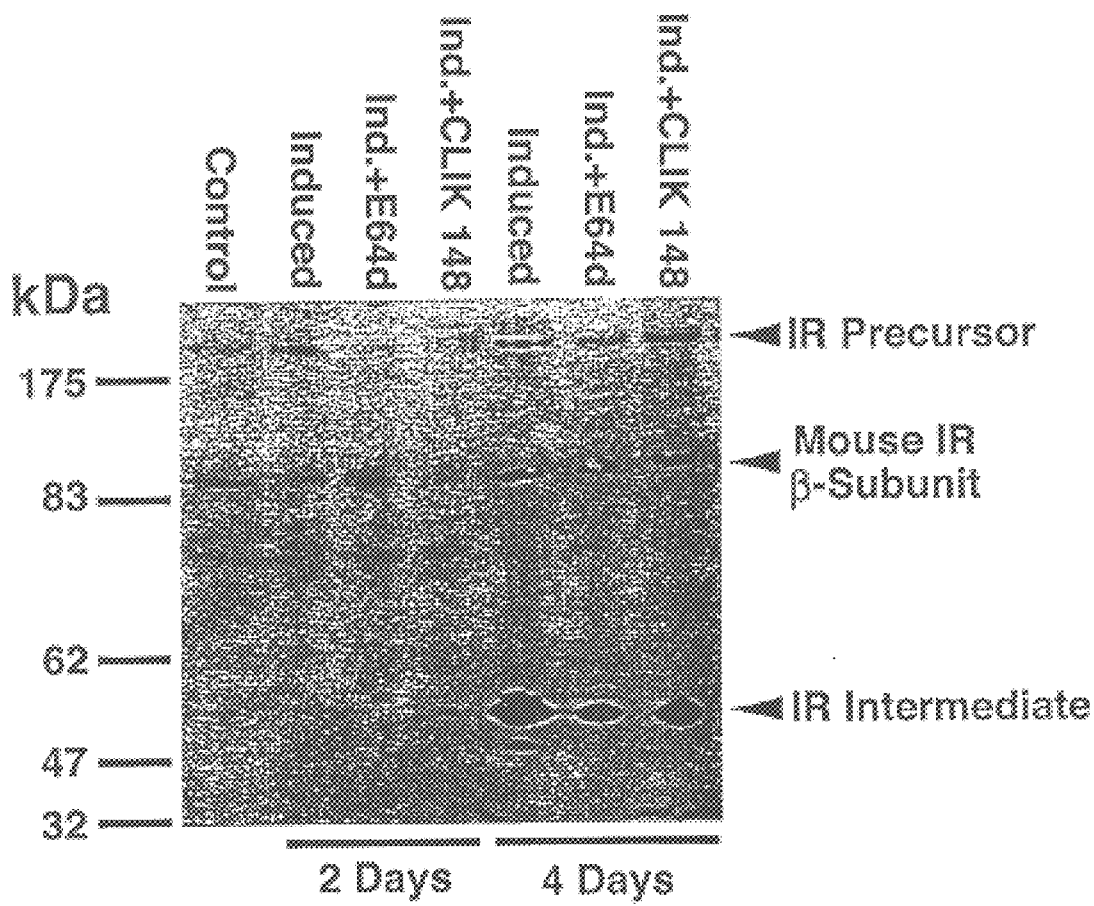
Fig 11. Decreased formation of mouse insulin receptor degradative intermediate in mouse 3T3-L1 cells treated with cathepsin L inhibitors.

SEQUENCE LISTING

<160> NUMBER OF SEQ ID NOS: 11

<210> SEQ ID NO 1
<211> LENGTH: 1575
<212> TYPE: DNA
<213> ORGANISM: Homo sapiens

<400> SEQUENCE: 1

```
agaaccgcga cctccgcaac cttgagcggc atccgtggag tgcgcctgca gctacgaccg      60
cagcaggaaa gcgccgccgg ccaggcccag ctgtggccgg acagggactg gaagagagga     120
cgcggtcgag taggtgtgca ccagccctgg caacgagagc gtctaccccg aactctgctg     180
gccttgaggt ggggaagccg gggagggcag ttgaggaccc cgcggaggcg cgtgactggt     240
tgagcgggca ggccagcctc cgagccgggt ggacacaggt tttaaaacat gaatcctaca     300
ctcatccttg ctgccttttg cctgggaatt gcctcagcta ctctaacatt tgatcacagt     360
ttagaggcac agtggaccaa gtggaaggcg atgcacaaca gattatacgg catgaatgaa     420
gaaggatgga ggagagcagt gtgggagaag aacatgaaga tgattgaact gcacaatcag     480
gaatacaggg aagggaaaca cagcttcaca atggccatga acgcctttgg agacatgacc     540
agtgaagaat tcaggcaggt gatgaatggc tttcaaaacc gtaagcccag gaaggggaaa     600
gtgttccagg aacctctgtt ttatgaggcc cccagatctg tggattggag agagaaaggc     660
tacgtgactc ctgtgaagaa tcagggtcag tgtggttctt gttgggcttt tagtgctact     720
ggtgctcttg aaggacagat gttccggaaa actgggaggc ttatctcact gagtgagcag     780
aatctggtag actgctctgg gcctcaaggc aatgaaggct gcaatggtgg cctaatggat     840
tatgctttcc agtatgttca ggataatgga ggcctggact ctgaggaatc ctatccatat     900
gaggcaacag aagaatcctg taagtacaat cccaagtatt ctgttgctaa tgacaccggc     960
tttgtggaca tccctaagca ggagaaggcc ctgatgaagg cagttgcaac tgtggggccc    1020
atttctgttg ctattgatgc aggtcatgag tccttcctgt tctataaaga aggcatttat    1080
tttgagccag actgtagcag tgaagacatg gatcatggtg tgctggtggt tggctacgga    1140
tttgaaagca cagaatcaga taacaataaa tattggctgg tgaagaacag ctggggtgaa    1200
gaatggggca tgggtggcta cgtaaagatg gccaaagacc ggagaaacca ttgtggaatt    1260
gcctcagcag ccagctaccc cactgtgtga gctggtggac ggtgatgagg aaggacttga    1320
ctggggatgg cgcatgcatg ggaggaattc atcttcagtc taccagcccc cgctgtgtcg    1380
gatacacact cgaatcattg aagatccgag tgtgatttga attctgtgat attttcacac    1440
```

-continued

```
tggtaaatgt tacctctatt ttaattactg ctataaatag gtttatatta ttgattcact    1500
tactgacttt gcattttcgt ttttaaaagg atgtataaat ttttacctgt ttaaataaaa    1560
tttaatttca aatgt                                                     1575
```

<210> SEQ ID NO 2
<211> LENGTH: 333
<212> TYPE: PRT
<213> ORGANISM: Homo sapiens

<400> SEQUENCE: 2

```
Met Asn Pro Thr Leu Ile Leu Ala Ala Phe Cys Leu Gly Ile Ala Ser
1               5                   10                  15

Ala Thr Leu Thr Phe Asp His Ser Leu Glu Ala Gln Trp Thr Lys Trp
            20                  25                  30

Lys Ala Met His Asn Arg Leu Tyr Gly Met Asn Glu Glu Gly Trp Arg
        35                  40                  45

Arg Ala Val Trp Glu Lys Asn Met Lys Met Ile Glu Leu His Asn Gln
    50                  55                  60

Glu Tyr Arg Glu Gly Lys His Ser Phe Thr Met Ala Met Asn Ala Phe
65                  70                  75                  80

Gly Asp Met Thr Ser Glu Glu Phe Arg Gln Val Met Asn Gly Phe Gln
                85                  90                  95

Asn Arg Lys Pro Arg Lys Gly Lys Val Phe Gln Glu Pro Leu Phe Tyr
            100                 105                 110

Glu Ala Pro Arg Ser Val Asp Trp Arg Glu Lys Gly Tyr Val Thr Pro
        115                 120                 125

Val Lys Asn Gln Gly Gln Cys Gly Ser Cys Trp Ala Phe Ser Ala Thr
    130                 135                 140

Gly Ala Leu Glu Gly Gln Met Phe Arg Lys Thr Gly Arg Leu Ile Ser
145                 150                 155                 160

Leu Ser Glu Gln Asn Leu Val Asp Cys Ser Gly Pro Gln Gly Asn Glu
                165                 170                 175

Gly Cys Asn Gly Gly Leu Met Asp Tyr Ala Phe Gln Tyr Val Gln Asp
            180                 185                 190

Asn Gly Gly Leu Asp Ser Glu Glu Ser Tyr Pro Tyr Glu Ala Thr Glu
        195                 200                 205

Glu Ser Cys Lys Tyr Asn Pro Lys Tyr Ser Val Ala Asn Asp Thr Gly
    210                 215                 220

Phe Val Asp Ile Pro Lys Gln Glu Lys Ala Leu Met Lys Ala Val Ala
225                 230                 235                 240

Thr Val Gly Pro Ile Ser Val Ala Ile Asp Ala Gly His Glu Ser Phe
                245                 250                 255

Leu Phe Tyr Lys Glu Gly Ile Tyr Phe Glu Pro Asp Cys Ser Ser Glu
            260                 265                 270

Asp Met Asp His Gly Val Leu Val Gly Tyr Gly Phe Glu Ser Thr
        275                 280                 285

Glu Ser Asp Asn Asn Lys Tyr Trp Leu Val Lys Asn Ser Trp Gly Glu
    290                 295                 300

Glu Trp Gly Met Gly Gly Tyr Val Lys Met Ala Lys Asp Arg Arg Asn
305                 310                 315                 320

His Cys Gly Ile Ala Ser Ala Ala Ser Tyr Pro Thr Val
                325                 330
```

<210> SEQ ID NO 3
<211> LENGTH: 1374
<212> TYPE: DNA
<213> ORGANISM: Mus musculus

<400> SEQUENCE: 3

```
cggcgacctc cggggatccg agtttgcaga cttcttgtgc gcacgtagcc gcctcaggtg      60
tttgaaccat gaatcttta ctccttttgg ctgtcctctg cttgggaaca gccttagcta     120
ctccaaaatt tgatcaaacc tttagtgcag agtggcacca gtggaagtcc acgcacagaa     180
gactgtatgg cacgaatgag gaagagtgga ggagagcgat atgggagaag aacatgagaa     240
tgatccagct acacaacggg gaatacagca cgggcagca cggcttttcc atggagatga     300
acgcctttgg tgacatgacc aatgaggaat tcaggcaggg ggtgaatggc tatcgccacc     360
agaagcacaa gaaggggagg cttttcagg aaccgctgat gcttaagatc cccaagtctg     420
tggactggag agaaaagggt tgtgtgactc ctgtgaagaa ccagggccag tgcgggtctt     480
gttgggcgtt tagcgcatcg ggttgcctag aaggacagat gttccttaag accggcaaac     540
tgatctcact gagtgaacag aaccttgtgg actgttctca cgctcaaggc aatcagggct     600
gtaacggagg cctgatggat tttgctttcc agtacattaa ggaaaatgga ggtctggact     660
cggaggagtc ttacccctat gaagcaaagg acggatcttg taaatacaga gccgagttcg     720
ctgtggctaa tgacacaggg ttcgtggata ccctcagca agagaaagcc ctcatgaagg     780
ctgtggcgac tgtggggcct atttctgttg ctatggacgc aagccatccg tctctccagt     840
tctatagttc aggcatctac tatgaaccca actgtagcag caagaacctc gaccatgggg     900
ttctgttggt gggctatggc tatgaaggaa cagattcaaa taagaataaa tattggcttg     960
tcaagaacag ctggggaagt gaatgggta tggaaggcta catcaaaata gccaaagacc    1020
gggacaacca ctgtggactt gccaccgcgg ccagctatcc tgtcgtgaat tgatgggtag    1080
cggtaatgag gacttatgga cactatgtcc aaaggaattc agcttaaaac tgaccaaacc    1140
cttattgagt caaccatgg tacttgaatc attgaggatc caagtcatga tttgaattct    1200
gttcccattt ttacatgggt taaatgttac cactacttaa aactcctgtt ataaacagct    1260
ttataatatt gaaaacttag tgcttaattc tgagtctgga atatttgttt tatataaagg    1320
ttgtataaaa ctttctttac ctcttaaaaa taaattttag ctcagtgtgt gtgt          1374
```

<210> SEQ ID NO 4
<211> LENGTH: 334
<212> TYPE: PRT
<213> ORGANISM: Mus musculus

<400> SEQUENCE: 4

```
Met Asn Leu Leu Leu Leu Ala Val Leu Cys Leu Gly Thr Ala Leu
1               5                   10                  15

Ala Thr Pro Lys Phe Asp Gln Thr Phe Ser Ala Glu Trp His Gln Trp
            20                  25                  30

Lys Ser Thr His Arg Arg Leu Tyr Gly Thr Asn Glu Glu Trp Arg
        35                  40                  45

Arg Ala Ile Trp Glu Lys Asn Met Arg Met Ile Gln Leu His Asn Gly
    50                  55                  60

Glu Tyr Ser Asn Gly Gln His Gly Phe Ser Met Glu Met Asn Ala Phe
65                  70                  75                  80

Gly Asp Met Thr Asn Glu Glu Phe Arg Gln Val Asn Gly Tyr Arg
            85                  90                  95
```

```
His Gln Lys His Lys Lys Gly Arg Leu Phe Gln Glu Pro Leu Met Leu
                100                 105                 110

Lys Ile Pro Lys Ser Val Asp Trp Arg Glu Lys Gly Cys Val Thr Pro
            115                 120                 125

Val Lys Asn Gln Gly Gln Cys Gly Ser Cys Trp Ala Phe Ser Ala Ser
130                 135                 140

Gly Cys Leu Glu Gly Gln Met Phe Leu Lys Thr Gly Lys Leu Ile Ser
145                 150                 155                 160

Leu Ser Glu Gln Asn Leu Val Asp Cys Ser His Ala Gln Gly Asn Gln
                165                 170                 175

Gly Cys Asn Gly Gly Leu Met Asp Phe Ala Phe Gln Tyr Ile Lys Glu
            180                 185                 190

Asn Gly Gly Leu Asp Ser Glu Glu Ser Tyr Pro Tyr Glu Ala Lys Asp
        195                 200                 205

Gly Ser Cys Lys Tyr Arg Ala Glu Phe Ala Val Ala Asn Asp Thr Gly
210                 215                 220

Phe Val Asp Ile Pro Gln Gln Glu Lys Ala Leu Met Lys Ala Val Ala
225                 230                 235                 240

Thr Val Gly Pro Ile Ser Val Ala Met Asp Ala Ser His Pro Ser Leu
                245                 250                 255

Gln Phe Tyr Ser Ser Gly Ile Tyr Tyr Glu Pro Asn Cys Ser Ser Lys
            260                 265                 270

Asn Leu Asp His Gly Val Leu Leu Val Gly Tyr Gly Tyr Glu Gly Thr
        275                 280                 285

Asp Ser Asn Lys Asn Lys Tyr Trp Leu Val Lys Asn Ser Trp Gly Ser
290                 295                 300

Glu Trp Gly Met Glu Gly Tyr Ile Lys Ile Ala Lys Asp Arg Asp Asn
305                 310                 315                 320

His Cys Gly Leu Ala Thr Ala Ala Ser Tyr Pro Val Val Asn
                325                 330

<210> SEQ ID NO 5
<211> LENGTH: 1484
<212> TYPE: DNA
<213> ORGANISM: Homo sapiens

<400> SEQUENCE: 5
agaaccgcga cctccgcaac cttgagcggc atccgtggag tgcgcctgca gctacgaccg      60
cagcaggaaa gcgccgccgg ccaggcccag ctgtggccgg acagggactg aagagagga     120 cgcggtcgag taggtgtgca ccagccctgg caacgagagc gtctacccgc aactctgctg    180
gccttgaggt ggggaagccg ggagggcag ttgaggaccc cgcggaggcg cgtgactggt    240
tgagcgggca ggccagcctc cgagccgggt ggacacaggt accgcagcca ggccggcgcc    300
aacgactcag ggcctggccc ggccagacag gaagctcag tccccgcacg ccagacagcg     360
gtactcctgc tggcgtcacc gcaaacatcc tctgaccgct acagccagtg tgtgggcagg    420
cgtcatgtcc ccgccctgc cacgcctgga gccctggaag ctggctgcag gctctggct     480 tcccgcgtgc gcccatatga ccccgtccct gatttagggg agcagtttgg ggtgtcggca    540
gcacaggccc aagtgaatga aggagggaag cagtgcgtgc tctccttccc agttttttcct   600 gggaaagcat tcagaaagg tttcatttaa gaagaggttg gggcggccag gtggctcact    660
cctgtaatcc cagcactttg ggaggctgag gtgggcggat cacctgaggt cagtagttca    720
gaccagcctg gccaacatgg tgaaacccc tctctactga aatacaaaa ttagacgggc     780
```

-continued

```
gaggcggcgc acgcctgtag ttccagctat tcaagaggct gaggaagaat ggcttgaacc    840
cgggaggcag aggttgctgt gagtcgatat cgcgccgttg aactccagcc tgggccacag    900
agcaagactc catctcaaaa aataaataaa taaataaata aataaataaa taggagagat    960
tggaaaactt atctcagctt ttggtgtttg ttagtcagga agatgtgtga aggcctccta   1020
actcttgggg atctctttgt cccctacttg ggaatcccac cttatcatta gtgaggtttt   1080
gcctgggcac gaaacctgga ttttttgcga ttggtacaaa acctggatca accgtttccc   1140
ggtttcctag ttgttgcctt aagcttctca cacacaaggt agtttcatac ggttctcata   1200
acctaaattg tcatcgcata aactgtttca gctcctacag ctctggacag gctgcttttc   1260
attttggtaa gtccatccag tacctccacg tgccctgttt ttctccaggc acatccttgg   1320
cctcttccac agtccttggg taaatgcttg ggagaataat ttaaatattt ttattctacc   1380
atggtggccc taatttttca gggggcagta agatggcttt ttaggattgg tctaatcaga   1440
tcctcatttt tgttcccttc ctaggtttta aaacatgaat ccta                     1484

<210> SEQ ID NO 6
<211> LENGTH: 1422
<212> TYPE: DNA
<213> ORGANISM: Mus musculus

<400> SEQUENCE: 6
gtacggctga ggtggaaatt ccacagcagg tcttttttt ctacgctttt cttacagaac      60
caaggcacca cgctggcgtg aaccctccaa agtggatcag cctcgcccca aggcttgcac    120
cacaggacag gttacgaccc ggcggcggtc acgcgcccgg actcccgcag gctccgcccc    180
gaggcaggca tagccaatga cggggcgggg gcgggccctg tcggggctgt agcctgagag    240 ccttttaaagc ctgagcccgg cgctgctcct ccagattctc ggacctcggc gacctccggg    300
gatccgagtt tgcagacttc ttgtgcgcag ctagccgcct caggtgagtg accccgcgg     360 gtttaaaggc ttcccgagca agggcaggta ggggaatcta aatgtgggga accatagcat    420
ctgcaacccg gactggagac ccccggatgg gccaggatct cgaggatgtg tcctcggcct    480
ccccgaagtg ataggcccctt gttgtcgagc ggggtcttca tcaggtcatg tgactccggg    540
ctgccgggac ccgtagggac agcgggaccc cctcaagctg gtcacgggac ccagggctcc    600
ttatgccgcc ataacattcg cgggcggtgg cccgagcgcg gagcggacgc ccatccccct    660
ctccccggaa cgggcccagc ttggccccta acccgaactg agatcgcata aggaggcatc    720
gccttgaggc ttcagttcgc ctgatgtgca gctgtgcgtt aaagtgtgtg gtggcagccc    780
accctctggg tattcctgta tgcccacttg gggtcactaa tacttgtcaa taaatgacct    840
ggacccagtt gtcctcttaa gattttgacg catacaatat cggaagactt aagactaccg    900
tggccctata ataagagaaa ggtgggggag gggggctgt cgagatggtt cagcgggtaa     960
gagcactgac cgttctttca aggtcctga gtgcaaatct cagcaaccac atggtggctc    1020
acaaccaccc ataatgagat ctgacaccct cttctagtgc gtcaaaaatc agctacagtg   1080
tacttatgta tgataataaa tcctaataaa taaaagagaa aagggtttat ccctgttcca   1140
atgactacta ggctgttttt gtttcagtag ctagagtcta gtaacctcca aagattaatt   1200
cctgacttgt ttttctccac tcataatcac atttgttaac acgtgcaagg atgcttcaac   1260
tcagaacggt ttactgctgg gctggtggct catggatccc taaacttgag agatgggtca   1320
ttgaaaaagt ttaaagcctg aactacatga gaaactgtcc ttaaaagaga aagcttccgt   1380
gggattctca tttcctcttt ttccttccct aggtgtttga ac                      1422
```

```
<210> SEQ ID NO 7
<211> LENGTH: 13
<212> TYPE: PRT
<213> ORGANISM: Homo sapiens

<400> SEQUENCE: 7

Thr Ser Glu Glu Phe Arg Gln Val Met Asn Gly Phe Gln
1               5                   10

<210> SEQ ID NO 8
<211> LENGTH: 4
<212> TYPE: PRT
<213> ORGANISM: Homo sapiens

<400> SEQUENCE: 8

Phe Tyr Lys Glu
1

<210> SEQ ID NO 9
<211> LENGTH: 18
<212> TYPE: PRT
<213> ORGANISM: Homo sapiens

<400> SEQUENCE: 9

Tyr Ser Val Ala Asn Asp Thr Gly Phe Val Asp Ile Pro Lys Gln Glu
1               5                   10                  15

Lys Ala

<210> SEQ ID NO 10
<211> LENGTH: 4
<212> TYPE: PRT
<213> ORGANISM: Homo sapiens

<400> SEQUENCE: 10

Ile Pro Lys Gln
1

<210> SEQ ID NO 11
<211> LENGTH: 10
<212> TYPE: PRT
<213> ORGANISM: Mus musculus

<400> SEQUENCE: 11

His Cys Gly Leu Ala Thr Ala Ala Ser Tyr
1               5                   10
```

METHOD FOR REDUCING BLOOD INSULIN LEVELS BY REDUCING IN VIVO CATHEPSIN L ACTIVITY

RELATIONSHIP TO CO-PENDING APPLICATIONS

This application is a continuation of U.S. patent application Ser. No. 09/784,646 filed on Feb. 14, 2001 and U.S. patent application Ser. No. 09/784,641 filed on Feb. 14, 2001, each of which is incorporated herein by reference.

BACKGROUND OF THE INVENTION

1. Field of the Invention

This invention relates to treatment of obesity and related diseases, such as hyperinsulinmia, hyperglycermia, hypertension, cardiovascular diseases, muscular dystrophy and infertility. More particularly, the invention relates to methods of treating obesity and non-insulin-dependent (type II) diabetes mellitus (NIDDM) by specifically targeting the genes and gene products of cathepsins.

2. Description of Related Art

Obesity is the most important nutritional disorder in the western world, with the estimates of its prevalence ranging from 30% to 50% within the middle-aged population. Obesity is usually defined as a body weight more than 20% in excess of the ideal body weight. Severe obesity can be a chronic disease that affects an increasingly large number of people and requires long-term treatment to promote and sustain weight loss.

Obesity is caused by accumulation of excess adipose tissue containing fat cells, or adipocytes, most predominately under the skin, in the abdominal cavity, in skeletal muscle, round the blood vessels, and in mammary gland. The adipose tissue of a normal 70-kg man contains about 15 kg of fat.

Adipocytes are developed from fibroblast-like cells, both during normal mammalian development and in various pathological circumstances for example, in muscular dystrophy, where the muscular cells die and are gradually replaced by fatty connective tissue. Adipocytes differentiation begins with the production of specific enzymes, followed by the accumulation of fat droplets, which then coalesce and enlarge until the cell is hugely distended, with only a thin rim of cytoplasm around the mass of lipid. Sul (1989) Curr. Opin. Cell Biol. 1:1116–1121.

Various factors influence the process of adipocyte differentiation. One of the factors was identified as growth hormone, a protein normally secreted into the bloodstream by the pituitary gland. But growth hormone is not the only secreted signaling molecule that regulates adipocyte development. Adipocyte precursors (preadipocites) that have been stimulated by growth hormone become sensitive to insulin-like growth fact-1 (IGF-1), which stimulates the proliferation of the differentiating fat cells. Recently, it has been found that integration of leptin, an adipocyte-derived hormone, in hypothalamic networks results in activation of peripheral metabolic pathways that control energy build-up and expenditure. Plasma leptin levels correlate with fat stores and respond to changes in energy balance. It was initially proposed that leptin serves a primary role as an anti-obesity hormone, and this role is commonly thwarted by leptin resistance. Ahima and Flier (2000) Annu. Rev. Physiol. 62:413–437.

Currently the medications most often used in the management of obesity are commonly known as "appetite suppressant" medications. Appetite suppressant medications promote weight loss by decreasing appetite or increasing the feeling of being full. These medication decrease appetite by increasing serotonin or catecholamine—two brain chemicals that affect mood and appetite. Examples of prescription appetite suppressant medications include dexfenfluramine (REDUX®), diethylpropion (TENUATE®, TENUATE DOSPAN®), fenfluramine (PONDIMIN®), mazindol (SANOREX®, MAZANOR®), phendimetrazine (BONTRIL®, PLEGINE®, PRELU-2®, X-TROZINE®), phentermine (ADIPEX-P®, FASTIN®, IONAMIN®, OBY-TRIM®), and sibutramien (MERIDIA®).

There are some potential side effects associated with long term use of these medications. For example, two FDA-approved appetite suppressant medications that affect serotonin release and reuptake have been withdrawn from the market (fenfluramine and dexfenfluramine). Medications that affect catecholamine levels (such as phentermine, diethylpropion, and mazindol) may cause symptoms of sleeplessness, nervousness, and euphoria. The primary known side effects of concern with sibutramine are elevation in blood pressure and pulse, which are usually small, but may be significant for people with poorly controlled high blood pressure, heart disease, irregular heart beat, or history of stroke.

Obesity is associated with an increased risk for cardiovascular diseases, diabetes, stroke, muscular dystrophy and infertility. In particular, obesity can evolve to type II diabetes in successive phases. Clinically, these phase can be characterized as normal glucose tolerance, impaired glucose tolerance, hyperinsulinemic diabetes, and hypoinsulinemic diabetes. Such a progressive impairment of glucose storage correlates with a rise in basal glycemia.

Generally, there are two major forms of diabetes mellitus: insulin-dependent (type I) and noninsulin-dependent diabetes mellitus (type-II). Type I diabetes, also called juvenile-onset diabetes mellitus, most often strikes suddenly in childhood. In contrast, type II diabetes, also called maturity-onset diabetes mellitus, usually develops rather gradually after the age of 40.

The polypeptide hormone insulin acts mainly on muscle, liver, and adipose tissue cells to stimulate the synthesis of glycogen, fats, and proteins while inhibiting the breakdown of these metabolic fuels. In addition, insulin stimulates the uptake of glucose by most cells, with the notable exception of brain and liver cells. Together with glucagon, which has largely opposite effects, insulin acts to maintain the proper level of blood glucose.

In diabetes, insulin either is not secreted in sufficient amounts or does not efficiently stimulate its target cells. As a consequence, blood glucose levels become so elevated that the glucose "spills over" into the urine, providing and convenient diagnostic test for the disease. Yet, despite of these high blood glucose levels, cells "starve" since insulin-stimulated glucose entry into the cells is impaired. Triacylglycerol hydrolysis, fatty acid oxidation, glucogeogenesis, and ketone body formation are accelerated, which eventually causes a decrease in blood volume, and ultimately life-threatening situations.

In type-I diabetes, insulin is absent or nearly so because the pancreas lacks or has defective β cells. This condition results from an autoimmune response that selectively destroy the β cells. Individuals with insulin-dependent diabetes requires regular insulin injections to survive and must follow carefully balanced diet and exercise regimens.

Type II diabetes or non-insulin-dependent diabetes mellitus, accounts for over 90% of the diagnosed cases of diabetes and affects more than 16 million people in the U.S. and some 200 million people around the world. Yousef et al. (1999) Diabetes Review 7: 55–76. Contrasting with type I diabetes, type II diabetic individuals have normal or even greatly elevated insulin levels. Their symptoms arise from an apparent paucity of insulin receptors on normally insulin-responsive cells. It has been hypothesized that the increased insulin production resulting from overeating, consequently obesity, eventually, suppresses the synthesis of insulin receptor.

Type II diabetes causes various disabling microvascular complications in patients. Besides retinopathy, nephropathy, and neuropathy, the disease is also associated with accelerated atherosclerosis and premature cardiovascular morbidity and mortality. This increased incidence of atherosclerosis (e.g., myocardial infarction, stroke, and peripheral vascular disease) is intricately associated with insulin resistance, which is a major pathophysiologic abnormality in type II diabetes. The insulin resistance of type II diabetes contributes to the metabolic abnormalities of hyperglycemia, hyperinsulinemia, dyslipidemia, hypertension, and hypercoaglulation.

The genetic basis for obesity and diabetes has been gradually unveiled in recent years. Zhang et al. cloned the mouse obesity (ob) gene and its human homologue in 1994. Zhang et al. (1994) Nature 372:425–432. Mutation in ob leads to symptoms of obesity. The extensively-studies animal models for genetic obesity are mice which contain the autosomal recessive mutations ob/ob and db/db. These mutations are on chromosomes 6 and 4, respectively, but lead to clinically similar symptoms of obesity, including hyperphageria, severe abnormalities in glucose and insulin metabolism, very poor thermo-regulation and non-shivering thermogenesis, and extreme torpor and underdevelopment of the lean body mass. Restriction of the diet of these animals to restore a more normal body fat mass to lean body mass ration is fatal and does not result in a normal habitus.

The products of the ob and db genes constitute a hormone/receptor pair (leptin and the leptin receptor, respectively). The ob/ob and db/db mice are unable to produce (ob/ob) or respond to (db/db) leptin, a peptide hormone produced by fat cells. When leptin is administered to ob/ob mice, the mice eat less, become more active, and lose a significant amount of weight.

In addition to ob and db, several other single gene mutations resulting in obesity in mice have been identified. For example, the yellow mutation at the agouti locus has been found to cause a pleiotropic syndrome which causes moderate adult onset obesity, a yellow coat color, and a high incidence of tumor formation (Herberg and Coleman (1977) Metabolism 26:59), and an abnormal anatomic distribution of body fat (Coleman (1978) Diabetologia 14:141–148). Additionally, mutations at the fat and tubby loci cause moderately severe, maturity-onset obesity with somewhat milder abnormalities in glucose homeostasis than are observed in ob and db mice. Coleman and Eicher (1990) J. Heredity 81:424–427. Further, autosomal dominant mutations at the adipose locus of chromosome 7, have been shown to cause obesity.

Other animal models include fa/fa (fatty) rats, which bear many similarities to the ob/ob and db/db mice. One difference is that, while fa/fa rats are very sensitive to cold, their capacity for non-shivering thermogenesis is normal. Torpor seems to play a larger part in the maintenance of obesity in fa/fa rats than in the mice mutants. In addition, inbred mouse strains such as NZO mice and Japanese KK mice are moderately obese. Certain hybrid mice, such as the Wellesley mouse, become spontaneously fat. Further, several desert rodents, such as the spiny mouse, do not become obese in their natural habitats, but do become so when fed on standard laboratory feed.

Animals which have, been used as models for obesity have also been developed via physical or pharmacological methods. For example, bilateral lesions in the ventromedial hypothalamus (VMH) and ventrolateral hypothalamus (VLH) in the rat are associated, respectively, with hyperphagia and gross obesity and with aphagia and cachexia. Further, it has been demonstrated that feeding monosodium-glutamate (MSG) to new born mice also results in an obesity syndrome.

Attempts have been made to utilize such animal models in the study molecular causes of obesity. For example, adipsin, a murine serine protease with activity closely similar to human complement factor D, produced by adipocytes, has been found to be suppressed in ob/ob, db/db and MSG-induced obesity. Flier (1987) Science 237:405. The suppression of adipsin precedes the onset of obesity in each model. Lowell (1990) Endocrinology 126:1514. Further studies have mapped the locus of the defect in these models to activity of the adipsin promoter. Platt (1989) Proc. Natl. Acad. Sci. USA 86:7490. Further, alterations have been found in the expression of neuro-transmitter peptides in the hypothalamus of the ob/ob mouse (Wilding (1993) Endocrinology 132:1939), of glucose transporter proteins in islet β-cells (Ohneda (1993) Diabetes 42:1065) and of the levels of G-proteins (McFarlane-Anderson (1992) Biochem. J. 282:15).

There still exists the need for improved treatment for obesity, diabetes and related diseases which have functional mechanisms different from those currently available.

SUMMARY OF THE INVENTION

The present invention relates to the discovery that certain cathepsins, particularly cathepsins L, K, and S, especially cathepsin L, play an important role in adipogenesis, a process of adipocyte or fat cell differentiation.

Leveraging the knowledge that the in vivo activity of fat regulating cathepsins, particularly cathepsins L, K, and S, especially cathepsin L, is tied to the regulation of fat storage, blood sugar levels and insulin levels, the present invention provides compositions, kits and methods for altering in vivo fat storage, blood sugar levels and/or insulin levels by altering the in vivo activity of fat regulating cathepsins. Such compositions, kits and methods may also be used to diagnose, monitor and treat various disease states which are related to improper, abnormal or undesirable fat storage levels, blood sugar levels and/or insulin levels.

In one embodiment, a method is provided for reducing fat storage in an animal comprising administering to the animal an agent which reduces an in vivo level of cathepsin L activity such that fat storage by the animal is reduced.

In another embodiment, a method is provided for reducing a blood sugar level of an animal comprising: administering to the animal an agent which reduces an in vivo level of cathepsin L activity such that the blood sugar level of the animal is reduced.

In yet another embodiment, a method is provided for reducing a blood insulin level of an animal comprising: administering to the animal an agent which reduces an in vivo level of cathepsin L activity such that the blood insulin level of the animal is reduced.

In yet another embodiment, a method is provided for treating an animal with one or more diseases selected from the group consisting of hyperinsulinmia, hyperglycermia, type II diabetes, hypertension, cardiovascular diseases, muscular dystrophy and infertility by administering to the animal an agent which reduces an in vivo level of cathepsin L activity.

These and other methods, compositions, and kits are described herein in greater detail.

DESCRIPTION OF FIGURES

FIG. 1. Cysteine protease inhibition profile by synthetic inhibitors in mouse peritoneal macrophages. [$^{125}$I]-Z-Tyr-Ala-CHN2-labeled mouse peritoneal macrophages were lysed and separated onto 12% SDS-PAGE to visualize labeled active cathepsins. Doses and inhibitors used were all indicated.

FIG. 2. Inhibition of cathepsin L resulted in accumulation of 95 kDa insulin receptor β subunits and their precursors. Human preadipocytes were incubated with and without inhibitors indicated at different doses, lysed, separated onto 7% SDS-PAGE, and probed with goat anti-human insulin receptor β-subunit polyclonal antibodies. Both mature β subunit and its precursor were indicated.

FIG. 3. Inhibition of human cathepsin L resulted in accumulation of 95 kDa insulin receptor like protein β subunit and its precursor. Cells were treated as in FIG. 2. Western blot analysis was performed using goat anti-human IGF-1R polyclonal antibodies.

FIG. 4. Inhibition of cathepsin L blocked the expression of CCAAT/enhancer-binding protein. Human preadipocytes were differentiated as in FIG. 2. A 10% gel was used to perform Western blot analysis using goat anti-human C/EBP-α polyclonal antibodies and the blot was detected using the corresponding HRP-conjugated secondary antibodies.

FIG. 5. Inhibition of cathepsin L blocked the expression of PPAR-γ. Human preadipocytes were used and Western blot analysis was performed as in FIG. 4 instead of using mouse anti-human PPAR-γ monoclonal antibodies as the primary antibodies.

FIG. 6. Oil-red staining of human preadipocytes and adipocytes. Cell differentiation was completely blocked by cathepsin L selective inhibitors CLIK 148 (10 μM) and 195 (10 μM) when these inhibitors were incubated with preadipocytes during the differentiation.

FIG. 7. Decreased cathepsin S and increased cathepsin L expression in differentiated human adipocytes. Cell lysates from both adipocytes (Induced) and preadipocytes (Control) were lysed, separated onto 12% SDS-PAGE, and stained with rabbit polyclonal antibodies against human cathepsins S (top), L (bottom), and K (not shown). No signals were detected for cathepsin K in either control or induced cells.

FIG. 8. Cathepsins L and S expression during mouse 3T3-L1 preadipocyte differentiation. Mouse 3T3-L1 cells were differentiated and cells were collected at different days during the differentiation. Lysates were separated on 12% SDS-PAGE and Western blot analysis was performed using rabbit polyclonal antibodies against cathepsins S and L (cross reactive with mouse gene products).

FIG. 9. Effect of cathepsin L inhibitor during mouse 3T3-L1 preadipocyte differentiation. Mouse 3T3-L1 cells were induced for adipogenesis. CLIK 148 (10 μM) was skipped at different time points (days) during adipogenesis. Cells were stained with oil-red at the end of differentiation.

FIG. 10. Decreased expression of cathepsin K during mouse 3T3-L1 differentiation. Cells were collected during the differentiation, lysed, separated onto 12% SDS-PAGE, and stained with rabbit anti-cathepsin K antibodies. Mature form of cathepsin K (28 kDa) was indicated.

FIG. 11. Decreased formation of mouse insulin receptor degradative intermediate in mouse 3T3-L1 cells treated with cathepsin L inhibitors. Different doses of inhibitors were utilized to treat 3T3-L1 cells during adipogenesis. Cell lysates were prepared and separated onto 10% SDS-PAGE for Western blot analysis using goat anti-mouse IR-β subunits.

DETAILED DESCRIPTION OF THE INVENTION

The present invention relates to the discovery that certain cathepsins, particularly-cathepsins L, K, and S, especially cathepsin L, play an important role in adipogenesis, a process of adipocyte or fat cell differentiation. Applicants have observed that animals whose in vivo cathepsin L activity have been reduced have much reduced ability to store fat than animals with normal cathepsin L activity levels. It is noted that cathepsins K and S share significant homology with cathepsin L and thus are also believed to have in vivo functionality related to fat storage regulation. It is further noted that other cathepsins, most likely those with similar homology to cathepsins L, K and S, particularly cathepsin L, may also exist which are involved in the regulatory pathway of fat storage. As a group, cathepsins which are involved with fat storage regulation are referred to herein as "fat regulating cathepsins."

A series of biochemical studies of adipocyte differentiation using inhibitors selectively targeting different forms of cathepsin were performed and suggest that cathepsin L is intimately involved in the turnover of the complex between insulin and insulin receptor (IR complex). Compared with the non-differentiated human cells (preadipocytes), the activity of cathepsin L increases after the differentiation of human adipocytes. Inhibition of cathepsin L resulted in accumulation of intact insulin receptor and insulin-like receptor in human preadipocytes, and lowered the levels of degraded insulin receptor intermediates in mouse preadipocytes. Further, such inhibition completely blocked both mouse and human preadipocyte adipogenesis. The details of the biochemical studies are described in the "Examples" section below.

Leveraging the knowledge that the in vivo activity of fat regulating cathepsins, particularly cathepsins L, K, and S, especially cathepsin L, is tied to the regulation of fat storage, blood sugar levels and insulin levels, the present invention provides compositions, kits and methods for altering in vivo fat storage, blood sugar levels and/or insulin levels by altering the in vivo activity of fat regulating cathepsins. Such compositions, kits and methods may also be used to diagnose, monitor and treat various disease states which are related to improper, abnormal or undesirable fat storage levels, blood sugar levels and/or insulin levels. For example, the present invention provides compositions useful for treating obesity, diabetes and other diseases which are related to undesirable or abnormal in vivo fat storage, blood sugar levels and/or insulin levels.

Without being bound by theory, by reducing the in vivo activity of fat regulating cathepsins in an animal, the process of differentiation from preadipocytes to adipocytes (adipogenesis) in that animal may be controlled, and likely the process of IR complex turnover. As a result, reducing the in vivo activity of fat regulating cathepsins, especially cathepsin L, can be employed according to the present invention to treat obesity, diseases associated with insulin recycling such as hyperinsulinmia, hyperglycermia, type II diabetes, and obesity-related diseases such as hypertension, cardiovascular diseases, muscular dystrophy and infertility.

A wide variety of therapeutic agents are provided and can be further developed to target fat regulating cathepsins, especially cathepsin L. These therapeutic agents may be designed to target fat regulating cathepsins by having an in vivo activity which reduces the expression of fat regulating cathepsins, increases the expression of fat regulating cathepsins.

The therapeutic agents may target fat regulating cathepsins based on the cDNA or regulatory regions of the fat regulating cathepsins. For example, DNA-based therapeutic agents, such as antisense inhibitors and ribozymes, can be utilized to target both the introns and exons of the cathepsin genes as well as at the RNA level.

Alternatively, the therapeutic agents may target fat regulating cathepsins based on the amino acid sequences including the propieces and/or three-dimensional protein structures of the fat regulating cathepsins. Protein-based therapeutics, such as human antibody, non-human monoclonal antibody and humanized antibody, can be used to specifically target different epitopes on a fat regulating cathepsin. Peptides or peptidomimetics can serve as high affinity inhibitors to specifically bind to the active site of a particular cathepsin, thereby inhibiting the in vivo activity of the cathepsin. Small molecules may also be employed to target cathepsin, especially those having high selectivity toward cathespin L.

In addition to targeting fat regulating cathepsins, therapeutic agents may also be used which competitively inhibit fat regulating cathepsins by competing with the natural substrates of cathepsins for binding with the enzymes.

The therapeutic agents which target fat regulating cathepsins are preferably more selective for fat regulating cathepsins than non-fat regulating cathepsins. In one embodiment, the therapeutic agents more selectively target cathepsins L, K, or S than other non-fat regulating cathepsins. In another embodiment, the therapeutic agents more selectively target cathepsin L than other non-fat regulating cathepsins. In yet another embodiment, the therapeutic agents more selectively target cathepsin L than cathepsins K or S.

With regard to the above, it is noted that "more selectively target", unless otherwise specified, may refer to "more selectively inhibiting expression of", "more selectively binding to", and/or "more significantly reducing the in vivo activity of."

When more selective targeting refers to an agent having a greater ability to reduce the in vivo activity of a particular cathepsin or class of cathepsins, this greater ability to reduce the in vivo activity may be measured based on a measure of the agent's ability to change the cathepsin's activity.

In embodiments where the agent binds to a cathepsin protein, the binding affinity of the agent to the cathepsin protein can be used as a test for greater selectivity. In such embodiments, the therapeutic agents which target fat regulating cathepsins preferably have a greater binding affinity to fat regulating cathepsins than non-fat regulating cathepsins. In one embodiment, the therapeutic agents have a greater binding affinity to cathepsins L, K, or S than other non-fat regulating cathepsins. In another embodiment, the therapeutic agents have a greater binding affinity to cathepsin L than other non-fat regulating cathepsins. In yet another embodiment, the therapeutic agents have a greater binding affinity to cathepsin L than cathepsins K or S. In one particular embodiment, the therapeutic agents more selectively target a particular cathepsin or class of cathepsins, (such as cathepsin L) than another particular cathepsin or class of cathepsins in the sense that the therapeutic agents have at least 10 times, more preferably at least 100 times, and most preferably at least 1000 times greater binding affinity to the particular cathepsin or class of cathepsins. For example, an agent may have at least 10 times, more preferably at least 100 times, and most preferably at least 1000 times greater binding affinity for cathepsin L than cathepsins K or S.

It is noted that the various therapeutic agents which target fat regulating cathepsins may be incorporated into various pharmaceutical formulations for administration to an animal to perform these functions. These pharmaceutical formulations may be include one or more suitable pharmaceutical carriers. The pharmaceutical formulations may be administered in any medically suitable manner, for example parenterally (e.g., intravenously, intraperitoneally, intrathecally or intramuscularly), transdermally, or orally.

The present invention provides a wide variety of methods for using the therapeutic agents which selectively target fat regulating cathepsins. These methods may be used with any type of animal. In one embodiment, the animal is a vertebrate. In another embodiment, the animal is a mammal. Specific examples of animals with which the methods, compositions and kits of the present invention may be used include, but are not limited to humans; pets, such as cats, dogs, and horses; livestock, such as chickens, turkeys, ostriches, ducks, geese, cattle, pigs, and horses; and animals that might be held in a zoo.

By using the therapeutic agents which selectively target fat regulating cathepsins, the therapeutic agents may reduce the fat regulating cathepsin activity of an animal in vivo (also referred to herein as "in vivo fat regulating cathepsin activity"). This may arise from a reduction in the amount of fat regulating cathepsin expressed by the animal or an inhibition of the fat regulating cathepsin expressed by the animal.

In one embodiment, a method is provided for reducing fat storage in an animal by administering to the animal an agent which reduces in vivo fat regulating cathepsin activity such that fat storage in the animal is reduced. The method may optionally further comprise measuring in vivo fat regulating cathepsin activity and adjusting the administration of the agent based on the measured in vivo activity. By reducing fat regulating cathepsin activity, such as the activity of cathepsin L, preadipocyte adipogenesis may be blocked by inhibiting differentiation of preadipocytes to adipocyte, causing a reduction of fat storage in the animal being treated with the agent.

In one embodiment, a method is provided for lowering a blood sugar level of an animal by administering to the animal an agent which reduces in vivo fat regulating cathepsin activity such that the blood sugar level of the animal is lowered. The method may optionally further comprise measuring the blood sugar level of the animal and/or the in vivo fat regulating cathepsin activity of the animal. Optionally, the administration of the agent may be adjusted based on one or both of these measurements.

The method is preferably performed on a human, more preferably a human having an elevated blood sugar level as compared to normal (e.g. higher than 1.26 grams of glucose per liter of blood), and most preferably an individual inflicted with type II diabetes.

By reducing fat regulating cathepsin activity, such as the activity of cathepsin L, proteolytic destruction of insulin receptor and insulin-like receptor may be prevented or significantly reduced to yield intact receptors. It has been found that the major cause of type II diabetes is insulin resistance and mutations in insulin receptor can cause insulin resistance or non-responsiveness to insulin administration. Individuals having insulin resistance develop diabetes despite of extraordinarily high plasma insulin concentration. Taylor et al. (1994) Diabetes 43:735–740. Thus, increasing the concentrations of intact insulin receptor and insulin-like receptor would promote insulin responsiveness and reduce blood sugar concentration, thereby alleviating symptoms of diabetes.

In yet another embodiment, a method is provided for lowering a blood insulin level of an animal by administering to the animal an agent which reduces in vivo fat regulating cathepsin activity such that the blood insulin level of the animal is lowered. The method may optionally further comprises measuring the blood insulin level of the animal and/or the in vivo fat regulating cathepsin activity of the animal. Optionally, the administration of the agent may be adjusted based on one or both of these measurements. The method is preferably performed on a human, more preferably a human having hyperinsulinmia, and most preferably a human inflicted with type II diabetes.

In yet another embodiment, a method is provided for treating an animal having a disease such as obesity, diseases associated with insulin recycling such as hyperinsulinmia, hyperglycermia, type II diabetes, or obesity-related diseases such as hypertension, cardiovascular diseases, muscular dystrophy and infertility. The method comprises administering to the animal an agent which reduces in vivo fat regulating cathepsin activity such that the blood insulin level of the animal is lowered. The method may optionally further comprise measuring the blood sugar level of the animal, the blood insulin level of the animal, and/or the in vivo fat regulating cathepsin activity of the animal. Optionally, the administration of the agent may be adjusted based on one or both of these measurements.

With regard to any of the above method embodiments, the agents which reduce fat regulating cathepsin activity in vivo preferably more significantly reduce the in vivo activity of fat regulating cathepsins than non-fat regulating cathepsins. In one variation, the agents more significantly reduce the in vivo activity of cathepsins L, K, or S than other non-fat regulating cathepsins. In another embodiment, the agents more significantly reduce the in vivo activity of cathepsin L than other non-fat regulating cathepsins. In yet another embodiment, the agents more significantly reduce the in vivo activity of cathepsin L than cathepsins K or S.

In one particular embodiment, the agents more selectively bind to cathepsin L than cathepsins K or S in the sense that the therapeutic agents have at least 10 times, more preferably at least 100 times, and most preferably at least 1000 times greater binding affinity for cathepsin L than cathepsins K or S.

With regard to the above, it is noted that more significantly reducing the in vivo activity of a particular cathepsin may relate to a more significant reduction in the expression of a particular cathepsin or may relate to a more significant reduction of the in vivo activity of a particular expressed cathepsin.

The present invention also relates to methods for diagnosing a disease state related to an improper, abnormal or undesirable fat storage level, blood sugar level and/or insulin level by measuring an amount of mRNA of a fat regulating cathepsin, such as cathepsin L; an amount expressed of a fat regulating cathepsin, such as cathepsin L; and/or a concentration of a fat regulating cathepsin, such as cathepsin L. It is noted that one or more fat regulating cathepsins may be monitored in combination including, for example, monitoring cathepsin L and K, L and S, or L, K, and S.

The present invention also relates to methods for diagnosing a cause of a disease state as being related to an improper, abnormal or undesirable fat storage level, blood sugar level and/or insulin level by measuring an amount of mRNA of a fat regulating cathepsin, such as cathepsin L; an amount expressed of a fat regulating cathepsin, such as cathepsin L; and/or a concentration of a fat regulating cathepsin, such as cathepsin L.

The present invention also relates to methods for detecting a genetic predisposition of an animal to develop a disease state related to an improper, abnormal or undesirable fat storage level, blood sugar level and/or insulin level by measuring an amount of mRNA of a fat regulating cathepsin, such as cathepsin L; an amount expressed of a fat regulating cathepsin, such as cathepsin L; and/or a concentration of a fat regulating cathepsin, such as cathepsin L.

With regard to each of the above diagnosis methods, the measurement that is made relative to a fat regulating cathepsin, such as cathepsin L may be used in combination with a measurement of a blood sugar level, an insulin level and/or a fat content of the animal. For example, an animal with increased or abnormally high cathepsin L activity may also have a higher fat content (or BMI, body mass index) in the animal. The combination of both a high cathepsin L activity (or concentration) and a high fat content can be used to identify a likely cause for the high fat content.

In one specific embodiment, the method comprises: measuring the activity of gene expression of a fat regulating cathepsin (such as cathepsin L) of the animal, wherein abnormally high activity of fat regulating cathepsin gene expression indicates that the animal is genetically predisposed of obesity. Activity of gene expression of the fat regulating cathepsin includes, but is not limited to, transcriptional activity such as binding of transcription factor(s) to the promoter region of the fat regulating cathepsin gene and transcribing mRNA, translational activity such as production of the fat regulating cathepsin protein, and post-translational activity such as proteolytic processing of the precursor of the fat regulating cathepsin, differential expression of endogenenous inhibitors of the fat regulating cathepsin (e.g., cystatins and saxiphilin).

In another specific embodiment, the method comprises: measuring the activity of gene expression of a fat regulating cathepsin (such as cathepsin L) of the animal; and measuring the blood sugar and/or insulin levels of the animal, wherein abnormally high activity of the fat regulating cathepsin gene expression and abnormally high blood sugar and/or insulin levels indicate that the animal is genetically predisposed of hyperinsulinmia or type II diabetes.

In yet another specific embodiment, the method comprises: measuring the activity of gene expression of the fat regulating cathepsin (such as cathepsin L) of the animal; and measuring the blood sugar and/or insulin levels of the animal, wherein abnormally high activity of the fat regulating cathepsin gene expression and abnormally high blood sugar and/or insulin levels indicate that the animal is genetically predisposed of hyperinsulinmia or type II diabetes.

The present invention also provides methods for screening for compounds or agents that modulate adipogenesis by interfering with the expression or activity of fat regulating cathepsins, preferably cathepsins K, L and S, more preferably cathepsins K and L, and most preferably cathepsin L.

In one embodiment, the method for screening for agents that inhibit adipogenesis in a cell-based system is provided. The method comprises: contacting cells containing preadipocytes with a test agent; and detecting levels of differentiation from preadipocytes to adipocytes, wherein a decrease in the level of preadipocyte differentiation indicates the test compound inhibits adipogenesis. In one variation, the method further comprises detecting the activity of one or more fat regulating cathepsins, a decrease in the activity of one or more of the fat regulating cathepsins correlating to a decrease in the level of preadipocyte differentiation. In another variation, the method further comprises detecting a decrease in gene expression of one or more fat regulating cathepsins, a decrease in the gene expression of one or more of the fat regulating cathepsins correlating to a decrease in the level of preadipocyte differentiation.

The activity of the fat regulating cathepsin includes, but is not limited to, its enzymatic activity and gene expression activity described above. The levels of preadipocyte differentiation include, but are not limited to, numbers of differentiated cells (i.e., adipocytes), levels of insulin receptor (e.g., insulin receptor $\beta$ subunit) and its precursor, levels of insulin receptor like $\beta$ subunit and its precursor, and levels of expression of the CCAAT/enhancer-binding protein $\alpha$ and PPAR-$\gamma$.

The present invention also provides methods for producing non-human animals with altered body fat content, such as livestock with a desired less or more fat content, by modifying the in vivo activity of one or more fat regulating cathepsins, preferably cathepsins K, L and S, more preferably cathepsins K and L, and most preferably cathepsin L.

In one embodiment, a method is provided for decreasing fat storage of an animal. The method comprising: administering to the animal an agent which decreases the activity of the fat regulating cathepsin in the animal, such that the fat content of the animal is reduced.

In another embodiment, a method is provided for increasing fat storage of an animal. The method comprising: administering to the animal an agent which increases the activity of the fat regulating cathepsin in the animal, such that the fat content of the animal is increased. The animal may be any vertebrate, preferably mammals, and more preferably livestock such as chickens, ducks, turkeys, ostriches, cattles, pigs, and horses. The animal may also be a pet such as a dog or a cat. Optionally, the agent is a fat regulating cathepsin, such as cathepsin L.

The present invention also provides compositions for reducing fat storage of an animal. The composition comprises: food for the animal and an agent that reduces the level of activity of a fat regulating cathepsin, such as cathepsin L, in the animal. For example, for a dog, the food can be dog food that contains an agent that reduces the level of activity of a fat regulating cathepsin. For a cat, the food can be cat food that contains an agent that reduces the level of activity of a fat regulating cathepsin. For livestock, such as horses, pigs, goats, sheet, etc., the food can be livestock feed to which an agent that reduces the level of activity of a fat regulating cathepsin has been added. Uptake of the composition may reduce fat absorption and storage through a reduction in the level of activity of the fat regulating cathepsin, thereby inhibiting adipogenesis mediated by the fat regulating cathepsin.

1. Cathepsins in the Cysteine Protease Superfamily

A "protease" is an enzyme which degrades proteins or peptides into smaller components by catalyzing hydrolysis of an amide bond, a process called proteolysis. The general mechanism that all proteases share in common in the proteolysis is that the catalysis is initiated by a nucleophilic attack on the carbonyl carbon of the amide bond. Different proteases utilize different strategies to produce the nucleophile and to juxtapose the nucleophile with the target bond. Based on these distinctions at the molecular level proteases are classified into 4 major classes: serine, cysteine, aspartate and metallo proteases. Serine and cysteine proteases utilize their hydroxyl and thiol groups of side chains, respectively, as nucleophiles directly, whereas aspartate and metallo proteases utilize aspartate residues and heavy metals, respectively, to immobilize and polarize a water molecule so that the oxygen atom in water becomes the nucleophile.

As described above, cysteine proteases are proteases which are distinguished by the presence of a cysteine residue in the active site of the protease which plays a critical role in the catalytic process. Numerous cysteine proteases have been identified in biological systems. Mammalian systems, including humans, normally degrade and process proteins via a variety of mechanisms including the actions of cysteine proteases. However, when present at elevated levels or when abnormally activated, or where introduced into a biological system in the context of a viral, bacterial or parasitic infection, cysteine proteases are thought to be involved in numerous pathophysiological processes and disease states. Intracellularly, they serve a variety of digestive and processing functions. Extracellularly, they may be involved in tissue remodeling and in pathologies such as arthritis, inflammation, myocardial infarction, Alzheimer's disease, cancer, muscular dystrophy, atherosclerosis, and aortic aneurysm.

Conventionally cysteine proteases are regarded as lysosomal mediators of terminal degration. However, more expansive roles have been implied for cysteine proteases in human biology. Some members in this super family have been found to be regulated with limited tissue expression and play important roles in cellular physiology such as apoptosis, prohormone processing, MHC class II immune responses, and extracellular matrix remodeling important to bone development.

Based on their distinct structures and functions, cysteine proteases are divided into two families: the family of enzymes related to interleukin 1$\beta$ converting enzyme (ICE), and the papain family. The ICE family of enzymes shares no sequence homology with the papain family, and have been implicated to play emerging roles in inflammation and programmed cell death (i.e., apoptosis). Henkart (1996) Immunity 4:194–201. ICE catalyzes the formation of interleukin-1$\beta$ (IL-1$\beta$), as well as the formation of interferon-$\gamma$ inducing factor (IGIF) from their inactive precursors, proIL-1$\beta$ and pro-IGIF, respectively. Interleukin-1$\beta$. is an immunoregulatory protein implicated in inflammation, diabetes, septic shock, rheumatoid arthritis and Alzheimer's disease. ICE and/or other caspases have also been linked to the apoptotic cell death of neurons which is implicated in a variety of neurodegenerative disorders including Parkinson's disease, ischemia and amyotrophic lateral sclerosis (ALS). Dinarello (1993) New Eng. J. Med., 328: 106–113.

Within the papain family of cysteine proteases, the calcium-activated neutral proteases ("calpains") comprise a group of intracellular cysteine proteases which are ubiquitously expressed in mammalian tissues. Activity of calpains is strictly calcium dependent but whose protease domain is nonetheless very much like that of papain. The calcium sensitivity results from the ancestral fusion of a papain-type protease domain with a calmodulin-like domain. Saido et al. (1994) FASEB J. 8:814–822.

Three major calpains have been identified: calpain I and II, and p94. The calpain family of cysteine proteases has been implicated in many diseases and disorders, including stroke, neurodegeneration, such as Alzheimer's disease, amyotrophy and motor neuron damage; acute central nervous system injury, muscular dystrophy, bone resorption, platelet aggregation, cataracts and inflammation. Calpain I has been implicated in excitatory amino-acid induced neurotoxicity disorders including ischemia, hypoglycemia and epilepsy. The cysteine protease p94, a muscle-specific member of the calpain family, has been identified as a gene product responsible for limb girdle muscular dystrophy. Barrett et al. (1996) ICOP Newsletter, 1–2.

Cathepsins are lysosomal cysteine proteases that belong to the papain family of cysteine protease superfamily. They are widely distributed and differentially expressed among tissues. These enzymes have a role in processes that involve proteolysis and turnover of specific proteins and tissues in local microenvironments. Cathepsins also initiate proteolytic cascades by proenzyme activation, participate in the expression of functional MHC class II molecules which bind to antigenic peptides, and process antigen in antigen-presenting cells. The various members of this family are differentially expressed, and some forms of cathepsins are closely associated with monocytes, macrophages, and other cells of the immune system. The secreted forms of several members of this family function in tissue remodeling through degradation of collagen, laminin, elastin, and other structural proteins and are implicated in inflammation associated with immunological response and in metastasis. Huisman et al. (1974) Biochem. Biophys. Acta 370:297–307; Mizuochi (1994) Immunol. Lett. 43:189–193; and Baldwin (1993) Proc. Natl. Acad. Sci. 90:6796–6800.

Abnormal regulation and expression of cathepsins is evident in various inflammatory disease states. In cells isolated from inflamed synovia, the mRNA for stromelysin, cytokines, TIMP-1, cathepsin, gelatinase, and other molecules is preferentially expressed. For example, expression of cathepsins L and D is elevated in synovial tissues from patients with rheumatoid arthritis and osteoarthritis. Cathepsin L expression may also contribute to the influx of mononuclear cells which exacerbates the destruction of the rheumatoid synovium. Keyszer (1995) Arthritis Rheum. 38:976–984.

The cathepsins have also been implicated in several other immune responses. In a rat model of human glomerular disease, the administration of a specific, irreversible inhibitor of cysteine protease (trans-epoxysuccinyl-L-leucylamido-(3-methyl)butane) significantly reduced proteinuria (Baricos, W. H. (1991) Arch. Biochem. Biophys. 288:468–72). The platelet aggregating cysteine protease implicated in thrombotic thrombocytopenic purpura shows the characteristics of a lysosomal cathepsin (Consonni, R. (1994) Br. J. Hematol. 87:321–324). In addition, the increased expression and differential regulation of the cathepsins is linked to the metastatic potential of a variety of cancers and as such is of therapeutic and prognostic interest (Chambers, A. F. et al. (1993) Crit. Rev. Oncog. 4:95–114).

There are many forms of lysosomal cysteine protease cathepsins so far characterized by standard protein isolation of enzyme activities and subsequent physical characterization, as well as by using techniques of molecular biology. Currently known forms of cathepsin include cathepsin B, C, F, H, J, K, L, M, O, Q, R, S, T, U, V, W and Z. It is possible that other forms of cathepsin may be identified in the future.

Among all forms of cathepsins, cathepsin B is the most abundant and widely expressed. Cathepsin B has weak endoprotease activity, but particularly good carboxypeptidase activity. Its primary role is to degrade unwanted or recycled proteins translocated into acidic compartments of endosomes and lysosomes. Cathepsin B's role appears to be reflected by the housekeeping nature of its promoter. It has been found to be highly expressed in solid tumors and thus has been implicated in tumor invading and metastasis. Yan et al. (1998) Biol. Chem. 379:113–123; and Berquin and Sloane (1996) Adv. Exp. Med. Biol. 389:281–294.

Cathepsin C (or dipeptidylpeptidase I) has been found to be a typical papain-type enzyme, albeit exhibiting only aminodipeptidase activity. McGuire et al. (1992) Arch. Biochem. Biophys. 295:280–288.

Cathepsin O is also a typical papain-type enzyme first isolated from a breast cancer cDNA library but then found to be widespread in its tissue distribution. Velasco et al. (1994) J. Biol. Chem. 269:27136–27146.

Cathepsin F shares about 58% homology with cathepsin W, about 42–43% with cathepsins L, K, S, H, and O, and 38% with cathepsin B. Cathepsin F is highly expressed in heart, skeletal muscle, brain, testis, and ovary; at moderate levels in prostate, placenta, liver, and colon; and at undetectable levels in peripheral leukocytes and thymus. Wang et al. (1998) J. Biol. Chem. 273:32000–32008.

Cathepsin K was first discovered as a cDNA prominent in rabbit osteoclasts and referred to as OC-2. Tezuka et al. (1994) J. Biol. Chem. 269:1106–1109. Cathepsin K is a typical cysteine protease with a signal peptide, short propiece, and a catalytic domain characteristic of the papain family. Expression of cathepsin K is both restricted and regulated. Cathepsin K is highly expressed in ovaries and osteoclasts (Bromme et al. (1996) J. Biol. Chem. 271:2126–2132), and a small amount of this enzyme is also found in human lung macrophages. Expression of cathepsin K appears to be upregulated at sites of inflammation.

Cathepsin K is the most potent mammalian elastase known to day. Other elastases, such as cathepsin S and L which share amino acid sequence homology to cathepsin K to some extent, are weaker than cathepsin K. Although more potent than cathepsin S or L, cathepsin K is not stable at neutral pH. The pH instability of cathepsin K is consistent with its primary function as a lysosomal enzyme and as the enzyme secreted into an acidic milieu by osteoclasts. It has been implicated that cathepsin K may play some roles in extracellular matrix remodeling and thus serves as a therapeutic target for treating bone disorders such as osteoporosis. Gelb et al . (1996) Science 273:1236–1238.

Cathepsin S was originally identified as a distinct enzyme having activity in lymph nodes and was found to be prominently expressed in and subsequently purified from spleen. Kirschke et al. (1989) Biochem. J. 264:467–473. As described above, cathepsin S is an elastase with substantial enzymatic activity and stability at neutral pH. This enzyme exhibited restricted and regulated tissue expression and was found to be inducible by cytokines such as interferon-γ and interleukin 1β. In rats, cathepsin S is expressed in thyroid tissue and is inducible by thyroid-stimulating hormone. Petanceska and Devi (1992) J. Biol. Chem. 267:26038–26043. Cathepsin S is also highly expressed in the spleen and antigen-presenting cells, including B lymphocytes, macrophages, and dendritic cells.

Cathepsin S has been found to play essential roles in class II antigen presentation based. This is consistent with the fact that it is highly expressed in spleen and lymph nodes and can be induced by cytokines known to be involved in major histocompatibility complex (MHC) class II antigen expression. Cathepsin S is involved in two steps of MHC class II antigen presentation pathway: 1) degradation of the MHC class II chaperone, the invariable chain (li), prior to its removal from the class II peptide binding cleft; and 2) the generation of antigenic peptides capable of replacing the invariant chain in the peptide-binding grove of the class II molecules. Studies suggest that cathepsin S acts on a relatively late li breakdown intermediate and is required for efficient proteolysis of li necessary for subsequent peptide loading. Inhibition or deficiency of cathepsin S resulted in impaired MHC class II processing and thus antigen presentation. It has been hypothesized that since cathepsin S played significant roles in antigen presentation it may serve as a target for developing therapeutics against diseases associated with exaggerated immune responses to exogenous antigens, such as asthma, transplant rejection, hypersensitivity pneumonitis, and possibly autoimmune diseases. Chapman et al. (1997) Ann. Rev. Physiol. 59:63–88.

Cathepsin L belongs to the group of elastases and shares higher amino acid sequence homology to cathepsin S and K than cathepsins B, F, H, and O. Due to its sequence homology to cathepsin K, cathepsin L has been implicated to play roles in bone formation and resorption, particularly in the decomposition of collagen, a bone-supporting protein. Woo et al. (1996) Euro. J. Pharmacol. 300:131–135; and Drake et al. (1996) J. Biol. Chem. 271:12511–12516.

The various cathepsin proteases differ in their gene structures and in their transcriptional regulation. The cathepsin L gene promoter has no TATA box but includes several SP-1 sites, two AP-2 transcription regulatory element binding sites, and a cAMP response element. Expression of cathepsin L can be induced by malignant transformation, growth factors, tumor promoters, and cyclic cAMP. Troen et al. (1991) Cell Growth Differ. 2:23–31. More recently, cathepsin L has been found to participate in the process of thymic epithelial cell li chain processing and thus affect the positive selection of CD4+ cells. Nakagawa et al. (1998) Science 280:450–453.

2. Agents that Target Fat Regulating Cathepsins

A wide variety of agents are provided and can be further developed to target fat regulating cathepsins, especially cathepsin L. These agents may be designed to target fat regulating cathepsins by having an in vivo activity which reduces the expression of fat regulating cathepsins, increases the expression of fat regulating cathepsins.

The agents may target fat regulating cathepsins based on the cDNA or regulatory regions of the fat regulating cathepsins. For example, DNA-based agents, such as antisense inhibitors and ribozymes, can be utilized to target both the introns and exons of the cathepsin genes as well as at the RNA level.

Alternatively, the agents may target fat regulating cathepsins based on the amino acid sequences including the propieces and/or three-dimensional protein structures of the fat regulating cathepsins. Protein-based agents, such as human antibody, non-human monoclonal antibody and humanized antibody, can be used to specifically target different epitopes on a fat regulating cathepsin. Peptides or peptidomimetics can serve as high affinity inhibitors to specifically bind to the active site of a particular cathepsin, thereby inhibiting the in vivo activity of the cathepsin. Small molecules may also be employed to target cathepsin, especially those having high selectivity toward cathespin L.

In addition to targeting fat regulating cathepsins, agents may also be used which competitively inhibit fat regulating cathepsins by competing with the natural substrates of cathepsins for binding with the enzymes.

a) Nucleic Acid-based Agents

Nucleic acid-based agents such as antisense molecules and ribozymes can be utilized to target both the introns and exons of the cathepsin genes as well as at the RNA level to inhibit gene expression thereof, thereby inhibiting the activity of the targeted cathepsin. Further, triple helix molecules may also be utilized in inhibiting the cathepsin gene activity. Such molecules may be designed to reduce or inhibit either the wild type cathepsin gene, or if appropriate, the mutant cathepsin gene activity. Techniques for the production and use of such molecules are well known to those of skill in the art, and are succinctly described below.

Antisense RNA and DNA molecules act to directly block the translation of mRNA by hybridizing to targeted mRNA and preventing protein translation. Antisense approaches involve the design of oligonucleotides that are complementary to a target gene mRNA. The antisense oligonucleotides will bind to the complementary target gene mRNA transcripts and prevent translation. Absolute complementarity, although preferred, is not required.

A sequence "complementary" to a portion of an RNA, as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. Wagner (1994) Nature 372:333–335.

For example, oligonucleotides complementary to either the 5'- or 3'-untranslated, non-coding regions of the human or mouse gene of cathepsin L could be used in an antisense approach to inhibit translation of endogenous cathepsin L mRNA. Table 1 lists the DNA sequences of the 5'-end untranslated regions of human [SEQ ID NO:5] and mouse [SEQ ID NO:6] cathepsin L.

Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of target gene mRNA, antisense nucleic acids are preferably at least six nucleotides in length, and are more preferably oligonucleotides ranging from 6 to about 50 nucleotides in length. In specific aspects the oligonucleotide is at least 10 nucleotides, preferably at least 17 nucleotides, more preferably at least 25 nucleotides and most preferably at least 50 nucleotides.

Alternatively, antisense molecules may be designed to target the translated region, i.e., the cDNA of the cathepsin gene. Table 1 lists the DNA sequence [SEQ ID NO: 1] and amino acid sequence [SEQ ID NO:2] of human cathepsin L, and the DNA sequence [SEQ ID NO: 3] and amino acid sequence [SEQ ID NO: 4] of mouse cathepsin L.

For example, the antisense RNA molecules targeting the full coding sequence or a portion of the mature murine cathepsin L (Kirschke et al. (2000) Euro. J. Cancer 36:787–795) may be utilized to inhibit expression of cathepsin L and thus reduce the activity of its enzymatic activity.

In addition, a full length or partial cathepsin L cDNA (Table 1) can be subcloned into a pcDNA-3 expression vector in reversed orientation and such a construct can be transfected into cells to produce antisense polyRNA to block endogenous transcripts of a cathepsin, such as cathepsin L, and thus inhibit the cathepsin's expression.

In vitro studies may be performed to quantitate the ability of the antisense oligonucleotide to inhibit gene expression. It is preferred that these studies utilize controls that distinguish between antisense gene inhibition and nonspecific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (See, e.g., Letsinger (1989) Proc. Natl. Acad. Sci. U.S.A. 86:6553–6556) or the blood-brain barrier (see, e.g., PCT Publication No. WO89/10134, published Apr. 25, 1988), hybridization-triggered cleavage agents. See, e.g., Krol (1988) Bio Techniques 6:958–976 or intercalating agents. See, e.g., Zon (1988) Pharm. Res. 5:539–549. The oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group consisting of, but not being limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group consisting of, but not being limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al. (1987) Nucl. Acids Res. 15:6625–6641). The oligonucleotide is a 2'-0-methylribonucleotide (Inoue et al. (1987) Nucl. Acids Res. 15:6131–6148), or a chimeric RNA-DNA analogue (Inoue et al. (1987) FEBS Lett. 215:327–330).

Oligonucleotides of the invention may be synthesized by standard methods known in the art, e.g. by use of an automated DNA synthesizer (such as are commercially available from Applied Biosystems, Inc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–7451), etc.

According to the present invention, the antisense molecules are delivered to cells which express a fat regulating cathepsin gene in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong pol III or pol III promoter. The use of such a construct to transfect target cells in the patient will result in the transcription of sufficient amounts of single stranded RNAs that will form complementary base pairs with the endogenous target gene transcripts and thereby prevent translation of the target gene mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Examples of viral vector include, but are not limited to viral vectors based on recombinant virus, such as modified or recombinant retrovirus, adenovirus, adeno-associated viruses, vaccinia virus, and herpes simplex virus.

Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon (1981) Nature 290:304–310), the promoter contained in the 3' long terminal repeat of Rous sarcoma virus (Yamamoto et al. (1980) Cell 22:787–797), the herpes thymidine kinase promoter (Wagner et al. (1981) Proc. Natl. Acad. Sci. U.S.A. 78:1441–1445), the regulatory sequences of the metallothionein gene (Brinster et al. (1982) Nature 296:39–42), etc. Any type of plasmid, cosmid, YAC or viral vector can be used to prepare the recombinant DNA construct which can be introduced directly into the tissue site. Alternatively, viral vectors can be used which selectively infect the desired tissue, in which case administration may be accomplished by another route (e.g., systemically).

Ribozyme molecules designed to catalytically cleave target gene mRNA transcripts can also be used to prevent translation of target gene mRNA and, therefore, expression of target gene product. See, e.g. Sarver et al. (1990) Science 247:1222–1225.

Ribozymes are enzymatic RNA molecules capable of catalyzing the specific cleavage of RNA. For a review, see Rossi (1994) Current Biology 4:469–471). The mechanism of ribozyme action involves sequence specific hybridization of the ribozyme molecule to complementary target RNA, followed by an endonucleolytic cleavage event. The composition of ribozyme molecules should include one or more sequences complementary to the target gene mRNA, and should include the well known catalytic sequence responsible for mRNA cleavage.

While ribozymes that cleave mRNA at site specific recognition sequences can be used to destroy target gene mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988 (Nature) 334:585–591.

Preferably, the ribozyme is engineered so that the cleavage recognition site is located near the 5' end of the target gene mRNA; i.e., to increase efficiency and minimize the intracellular accumulation of non-functional mRNA transcripts.

The ribozymes of the present invention also include RNA endoribonucleases such as the one which occurs naturally in *Tetrahymena thermophila* (known as the IVS, or L-19 IVS RNA) and which has been extensively described by Thomas Cech and collaborators. Zaug et al. (1984) Science 224:574–578; Zaug and Cech (1986) Science, 231:470–475; Zaug et al. (1986) Nature 324:429–433; Been and Cech (1986) Cell 47:207–216. This type of ribozymes have an eight base pair active site which hybridizes to a target RNA sequence whereafter cleavage of the target RNA takes place. The invention encompasses those ribozymes which target at lease eight base-pair sequences that are present in the cathepsin gene.

As in the antisense approach, the ribozymes can be composed of modified oligonucleotides (e.g. for improved stability, targeting, etc.) and should be delivered to cells which express the cathepsin gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous target gene messages and inhibit translation. Because ribozymes unlike antisense molecules, are catalytic, a lower intracellular concentration may be required for efficiency.

Endogenous cathepsin gene expression can also be reduced by inactivating or "knocking out" the targeted cathepsin gene or its promoter using targeted homologous recombination. Smithies et al. (1985) Nature 317:230–234; Thomas and Capecchi, (1987) Cell 51:503–512; and Thompson et al. (1989) Cell 5:313–321. For example, a mutant, non-functional target gene (or a completely unrelated DNA sequence) flanked by DNA homologous to the endogenous target gene (either the coding regions or regulatory regions of the target gene) can be used, with or without a selectable marker and/or a negative selectable marker, to transfect cells that express the target gene in vivo. Insertion of the DNA construct, via targeted homologous recombination, results in inactivation of the target gene. Such approaches are particularly suited in the agricultural field where modifications to ES (embryonic stem) cells can be used to generate animal offspring with an inactive target gene (e.g., see Thomas and Capecchi (1987) and Thompson (1989), supra). For example, cathepsin L gene of livestock can be knocked out to produce animals with lower body fat content. However this approach can be adapted for use in humans provided the recombinant DNA constructs are directly administered or targeted to the required site in vivo using appropriate viral vectors.

Alternatively, endogenous cathepsin gene expression can be reduced by targeting deoxyribonucleotide sequences complementary to the regulatory region of the cathepsin gene (i.e., the target gene promoter and/or enhancers) to form triple helical structures that prevent transcription of the target gene in target cells in the body. See generally, Helene (1991) Anticancer Drug Des. 6:569–584; Helene et al. (1992) Ann. N.Y. Acad. Sci. 660:27–36; and Maher (1992) Bioassays 14:807–815.

Nucleic acid molecules to be used in triplex helix formation for the inhibition of transcription should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, contain a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'–3', 3'14 5' manner, such that they base pair with first one strand of a duplex and then the other, eliminating the necessity for a sizeable stretch of either purines or pyrimidines to be present on one strand of a duplex.

In instances wherein the antisense, ribozyme, and/or triple helix molecules described herein are utilized to inhibit mutant gene expression, it is possible that the technique may so efficiently reduce or inhibit the transcription (triple helix)

and/or translation (antisense, ribozyme) of mRNA produced by normal target gene alleles that the possibility may arise wherein the concentration of normal target gene product present may be lower than is necessary for a normal phenotype. In such cases, to ensure that substantially normal levels of target gene activity are maintained, therefore, nucleic acid molecules that encode and express target gene polypeptides exhibiting normal target gene activity may, be introduced into cells via gene therapy methods that do not contain sequences susceptible to whatever antisense, ribozyme, or triple helix treatments are being utilized. Alternatively, in instances whereby the target gene encodes an extracellular protein, it may be preferable to coadminister normal target gene protein in order to maintain the requisite level of target gene activity.

Anti-sense RNA and DNA, ribozyme, and triple helix molecules of the invention may be prepared by any method known in the art for the synthesis of DNA and RNA molecules, as discussed above. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

b) Antibodies for Inhibition of Cathepsin Gene Products

Protein-based therapeutics, such as human antibody, non-human monoclonal antibody and humanized antibody, can be used to specifically target different epitopes on a fat regulating cathepsin.

Antibodies that are both specific for cathepsin gene protein and interfere with its activity may be used to inhibit cathepsin gene function. Where desirable, antibodies specific for mutant cathepsin protein which interfere with the activity of such mutant cathepsin product may also be used to inhibit cathepsin gene function. Such antibodies may be generated using standard techniques (briefly described below) against the cathepsins themselves or against peptides corresponding to portions of the cathepsins. The antibodies include but are not limited to polyclonal, monoclonal, Fab fragments, single chain antibodies, chimeric antibodies, etc.

Many methods have been developed for the production of antibodies capable of specifically recognizing one or more differentially expressed or pathway gene epitopes. Such antibodies may include, but are not limited to polyclonal antibodies, monoclonal antibodies (mAbs), humanized or chimeric antibodies, single chain antibodies, Fab fragments, F(ab')$_2$ fragments, fragments produced by a FAb expression library, anti-idiotypic (anti-Id) antibodies, and epitope-binding fragments of any of the above. Such antibodies may be used, for example, in the detection of a fingerprint, target, or pathway gene in a biological sample, or, alternatively, as a method for the inhibition of abnormal target gene activity. Thus, such antibodies may be utilized as part of body weight disorder treatment methods, and/or may be used as part of diagnostic techniques whereby patients may be tested for abnormal levels of fingerprint, target, or pathway gene proteins, or for the presence of abnormal forms of the such proteins.

For the production of antibodies to a cathepsin gene, various host animals may be immunized by injection with a cathepsin protein, or a portion thereof. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Polyclonal antibodies are heterogeneous populations of antibody molecules derived from the sera of animals immunized with an antigen, such as a cathepsin gene product, or an antigenic functional derivative thereof. For the production of polyclonal antibodies, host animals such as those described above, may be immunized by injection with a cathepsin gene product supplemented with adjuvants as also described above.

Monoclonal antibodies, which are homogeneous populations of antibodies to a particular antigen, may be obtained by any technique which provides for the production of antibody molecules by continuous cell lines in culture. These include, but are not limited to the hybridoma technique of Kohler and Milstein (1975) Nature 256:495–497; and U.S. Pat. No. 4,376,110, the human B-cell hybridoma technique (Kosbor et al. (1983) Immunology Today 4:72; Cole et al. (1983) Proc. Natl. Acad. Sci. USA 80:2026–2030, and the EBV-hybridoma technique (Cole et al. (1985) Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In a preferred embodiment, monoclonal antibodies against cathepsin L, procathepsin L or another fat regulating cathepsin are used as the genetic therapeutics for treating obesity and related diseases according to the present invention. Examples of such antibodies include, but are not limited to mouse monoclonal antibodies against cathepsin L generated by immunizing mice with purified human pre-cathepsin L. Weber et al. (1997) Hybridoma 16:159–166. Such antibodies are available from Labsoft Diagnostics AG, Germany, including clones CPLH2D4, CPLH33/1, CPLH33/2, and CLP1/36.

Clone #CPLH2D4 (isotype mouse IgG$_1$, kappa) recognizes epitope: T67 S E E F R Q V M N G F Q 79 [SEQ ID NO: 7] of the propeptide of human procathepsin L and does not recognize mature single or two chain cathepsin L.

Clone #CPLH33/1 (isotype mouse IgG$_1$, kappa) recognizes epitope: F241YKE244 [SEQ ID NO: 8] recognizes mature single or two chain cathepsin L.

Clone #CLP1/36 (isotype mouse IgG$_1$, kappa) is produced by immunizing mice with peptide Y200 S V A N D T G F V D I P K Q E K A217 [SEQ ID NO: 9] of human procathepsin L and recognizes epitope: I211PKQ214 [SEQ ID NO: 10] and also recognizes mature single or two chain cathepsin L.

Clone #CPLH3G10 (isotype mouse IgG$_1$, kappa) binds to epitope: H304 C G L A T A A S Y 313 [SEQ ID NO: 11] of mouse procathepsin L and recognizes mature single chain mouse cathepsin L and mature two chain mouse cathepsin L (light chain) and mouse procathepsin L. The antibody also recognizes mature human single chain cathepsin L, mature human two chain cathepsin L (light chain), human procathepsin L and rat cathepsin L (light chain).

In addition, techniques developed for the production of "chimeric antibodies" or "humanized antibodies" may be utilized to modify mouse monoclonal antibodies to reduce immunogenicity of non-human antibodies. Morrison et al. (1984) Proc. Natl. Acad. Sci. 81:6851–6855; Neuberger et al. (1984) Nature, 312:604–608; Takeda et al. (1985) Nature, 314:452–454. Such antibodies are generated by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird (1988) Science 242:423–426; Huston et al. (1988) Proc. Natl. Acad. Sci. USA 85:5879–5883; and Ward et al. (1989) Nature 334:544–546) can be adapted to produce differentially expressed or pathway gene-single chain antibodies. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al. (1989) Science 246:1275–1281) to allow rapid and easy identification of monoclonal Fab fragments with the desired specificity.

Since the target gene protein, cathepsin, is an intracellular enzyme and whole antibodies are used while internalizing antibodies may be preferred. However, lipofectin or liposomes may be used to deliver the antibody or a fragment of the Fab region which binds to the target gene product epitope into cells. Where fragments of the antibody are used, the smallest inhibitory fragment which binds to the target protein's binding domain is preferred. For example, peptides having an amino acid sequence corresponding to the domain of the variable region of the antibody that binds to the cathepsin may be used. Such peptides may be synthesized chemically or produced via recombinant DNA technology using methods well known in the art.

Alternatively, single chain neutralizing antibodies which bind to cathepsin epitopes may also be administered. Such single chain antibodies may be administered, for example, by expressing nucleotide sequences encoding single-chain antibodies within the target cell population by utilizing, for example, techniques such as those described in Marasco et al. Marasco, W. et al. (1993) Proc. Natl. Acad. Sci. USA 90:7889–7893.

c) Agents that Inhibit Expression or Synthesis of Cathepsin Genes

According to the present invention, adipogenesis may be modulated by using an agent that regulates expression of fat regulating cathepsin genes, preferably cathepsins K, L, and S, more preferably cathespins K and L, and most preferably cathepsin L.

A variety of techniques may be utilized to inhibit the expression of a fat regulating cathepsin gene and/or gene products, thereby inhibiting adipogenesis, which eventually ameliorates symptoms of obesity and related diseases such a type II diabetes and hypertension.

The level of gene activity may be inhibited, for example, by either lowering the levels of mRNA transcribed from the targeted cathepsin gene or by inhibiting translational and post-translation process of the cathepsin gene product.

Individuals inflicted with obesity, diabetes and related diseases may be treated by gene therapy. One or more copies of a gene or a portion of the gene that directs the production of a protein that interferes with transcription or translation machinery of the cathespin gene may be inserted into cells. Vectors that may be used for such gene therapy include, but are not limited to adenovirus, adeno-associated virus, and retrovirus vectors, in addition to other particles that introduce DNA into cells, such as liposomes.

For example, such techniques can be utilized to interfere with transcription of a fat regulating cathepsin, such as human cathepsin L. For example, 5' regulatory sequences (e.g., promoter/enhancer sequences) for human [SEQ ID NO: 5] and mouse cathepsin L [SEQ ID NO: 6] have been characterized in Chauhan et al. (1993) J. Biol. Chem. 268:1039–1045 (human); and Troen et al. (1991) Cell Growth Differ. 2:23–31 (mouse).

Additionally, antibodies may be administered which specifically bind to a protein, for example, transcription factor for human cathepsin L gene, to either directly or indirectly activate the cathepsin L function. Such antibodies can include, but are not limited to polyclonal, monoclonal, FAb fragments, single chain antibodies, chimeric antibodies and the like. The antibodies may be generated using standard techniques such as those described above in Section b), and may be generated against the protein themselves or against proteins corresponding to portions of the proteins. The antibodies may be administered, for example, according to the techniques described above, in Section b).

Additionally, any other compound identified which alters the level of cathepsin gene expression or the level of cathepsin gene product activity can be administered herein. Administration techniques can be as those described, below, in Section 3.

d) Agents that Inhibit Enzymatic Activity of Fat Regulating Cathepsin

Peptides or peptidomimetics can serve as high affinity inhibitors to specifically bind to the active site of a fat regulating cathepsin, thereby inhibiting the enzymatic activity of the cathepsin. Examples of inhibitors selective for cathepsin S, K, and L are listed in Tables 2, 3, and 4, respectively.

Additionally, prodomains of the cathepsins can serve as inhibitors of their parent enzymes. Isolated cathepsin prodomains are highly potent, noncovalent inhibitors selective for their mature enzymes. Guay et al. (2000) Euro. J. Biochem. 267:6311–6318. It has been demonstrated that human cathepsin L propeptide is 500-fold and at least 10,000-fold more selective for human cathepsin L than human cathepsin S and human cathepsin B, respectively. Carmona et al. (1996) Biochem. 35:8149–8157. A propeptide of liver fluke cathepsin L was found to be a highly selective inhibitor as compared with human cathepsin K, L, and B. QQQQ X-ray crystal structures of cathepsins B, L and K reveal that the prodomain folds back through the active site cleft of the enzyme, interacting with, and therefore blocking, both the prime and nonprime binding sites, as well as interacting with a loop on the mature enzyme known as the propeptide binding loop. Sivaraman et al. (1999) Protein Sci. 8:283–290; and Groves et al. (1998) Proteins 32:504–514. The direction of the prodomain through the active site is opposite to that of the natural substrates and hence the propeptide is not in the correct conformation to be cleaved by the active site residues.

The propeptides of cathepsin K, L, and S may be produced by expressing the peptide in *E. coli* cells by following the method described in Guay et al., supra. Other methods of peptide production such as chemical synthesis are known to one skilled in the art.

Additionally, small molecules may also be used to inhibit cathepsins. The small molecule inhibitor may have higher selectivity toward a particular form of cathepsin than other forms of cathepsin, or may only inhibit one form of cathepsin. Preferably, the small molecule has higher selectivity toward cathepsins L, K, and S than other forms of cathepsin. More preferably, the small molecule inhibitor has higher selectivity toward cathepsin L and K than other forms of cathepsin. Most preferably, the small molecule inhibitor has higher selectivity toward cathepsin L than other forms of cathepsin.

The small molecule inhibitor is preferably a stronger inhibitor of cathepsins L, K, or S than other non-fat regulating cathepsins. In one variation, the small molecule inhibitor is preferably a stronger inhibitor of cathepsin L than other non-fat regulating cathepsins. In another variation, the small molecule inhibitor is preferably a stronger inhibitor of cathepsin L than cathepsins K or S: In one particular variation, the small molecule inhibitor is preferably a stronger inhibitor of a particular cathepsin or class of cathepsins, (such as cathepsin L) than another particular cathepsin or class of cathepsins in the sense that the inhibitor has at least 10 times, more preferably at least 100 times, and most preferably at least 1000 times stronger inhibitor of the particular cathepsin or class of cathepsins. For example, an agent may be at least a 10 times, more preferably at least a 100 times, and most preferably at least a 1000 times stronger inhibitor of cathepsin L than cathepsins K or S.

Table 4 lists examples of small molecule, peptide, or peptidomimetics that may be used to inhibit cathespin L activity in the treatment of indications described herein. Tables 2 and 3 list examples of small molecule agent that may be used to specifically inhibit activity of cathepsin S and K, respectively. The inhibitory potencies ($K_i$, dissociation constants) for selected forms of cathepsin and references teaching the methods of synthesizing these agents are also listed in these tables.

3. Pharmaceutical Preparations and Methods of Administration

The compounds, nucleic acid molecules and viral vectors that inhibit cathepsin gene expression, synthesis and/or activity as described above can be administered to a patient at therapeutically effective doses to treat or ameliorate obesity, diabetes and related diseases. A therapeutically effective dose refers to that amount of the agent sufficient to result in amelioration of symptoms of obesity, diabetes and related diseases, or alternatively, to that amount of a nucleic acid molecule sufficient to express a concentration of gene product which results in the amelioration of such symptoms.

Toxicity and therapeutic efficacy of such agents can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Agents which exhibit large therapeutic indices are preferred. While agents that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the $IC_{50}$ (i.e., the concentration of the test agent which achieves a half-maximal inhibition of symptoms) as determined in cell culture. Such information can be used to more accurately determine useful doses in humans. Levels in plasma may be measured, for example, by high performance liquid chromatography.

Therapeutics for use in accordance with the present invention may be formulated in conventional manner to produce pharmaceutical compositions using one or more physiologically acceptable carriers or excipients.

Thus, the cathepsin inhibitors and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the pharmaceutical compositions for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The cathepsin inhibitors may be formulated for parenteral administration by injection, e.g., by bolus injection or continuous infusion. Formulations for injection may be presented in unit dosage form, e.g., in ampoules or in multidose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The cathepsin inhibitors may also be formulated in rectal compositions such as suppositories or retention enemas, e.g., containing conventional suppository bases such as cocoa butter or other glycerides.

In addition to the formulations described previously, the cathepsin inhibitors may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

4. Diagnosis of Genetic Predisposition of Obesity, Diabetes and Related Diseases The present invention also provides methods for diagnosing genetic predisposition of obesity and related diseases of an animal by specifically detecting and monitoring the activity of fat regulating cathepsins. Such fat regulating cathepsins may include cathepsins K, L and S, more preferably cathepsin K and L, and most preferably cathepsin L.

A variety of methods may be employed for detecting a genetic predisposition of an animal to develop a disease state related to an improper, abnormal or undesirable fat storage level, blood sugar level and/or insulin level by measuring an amount of mRNA of a fat regulating cathepsin, such as cathepsin L; an amount expressed of a fat regulating cathepsin, such as cathepsin L; and/or a concentration of a fat regulating cathepsin, such as cathepsin L.

The measurement that is made relative to a fat regulating cathepsin, such as cathepsin L may be used in combination with a measurement of a blood sugar level, an insulin level and/or a fat content of the animal. For example, an animal with increased or abnormally high cathepsin L activity may also have a higher fat content (or BMI, body mass index) in the animal. The combination of both a high cathepsin L activity (or concentration) and a high fat content can be used to identify a likely cause for the high fat content.

In one specific embodiment, the method comprises: measuring the activity of gene expression of a fat regulating cathepsin (such as cathepsin L) of the animal, wherein abnormally high activity of fat regulating cathepsin gene expression indicates that the animal is genetically predisposed of obesity. Activity of gene expression of the fat regulating cathepsin includes, but is not limited to, transcriptional activity such as binding of transcription factor(s) to the promoter region of the fat regulating cathepsin gene and transcribing mRNA, translational activity such as production of the fat regulating cathepsin protein, and post-translational activity such as proteolytic processing of the precursor of the fat regulating cathepsin, differential expression of endogenenous inhibitors of the fat regulating cathepsin (e.g., cystatins and saxiphilin).

In another specific embodiment, the method comprises: measuring the activity of gene expression of a fat regulating cathepsin (such as cathepsin L) of the animal; and measuring the blood sugar and/or insulin levels of the animal, wherein abnormally high activity of the fat regulating cathepsin gene expression and abnormally high blood sugar and/or insulin levels indicate that the animal is genetically predisposed of hyperinsulinmia or type II diabetes.

In yet another specific embodiment, the method comprises: measuring the activity of gene expression of the fat regulating cathepsin (such as cathepsin L) of the animal; and measuring the blood sugar and/or insulin levels of the animal, wherein abnormally high activity of the fat regulating cathepsin gene expression and abnormally high blood sugar and/or insulin levels indicate that the animal is genetically predisposed of hyperinsulinmia or type II diabetes.

The present invention also provides methods for diagnosing genetic predisposition of obesity, diabetes and related diseases of an animal by specifically detecting and monitoring the activity of fat regulating cathepsins, preferably cathepsins K, L and S, more preferably cathepsins K and L, and most preferably cathepsin L.

In one embodiment, the method comprises: measuring the activity of gene expression of a fat regulating cathepsin of the animal, wherein abnormally high activity of fat regulating cathepsin gene expression indicates that the animal is genetically predisposed of obesity. Activity of gene expression of the fat regulating cathepsin includes, but is not limited to, transcriptional activity such as binding of transcription factor(s) to the promoter region of fat regulating cathepsin gene and transcribing mRNA, translational activity such as production of the fat regulating cathepsin protein, and post-translational activity such as proteolytic processing of the precursor of the fat regulating cathepsin, differential expression of endogenenous inhibitors of fat regulating cathepsin (e.g., cystatins and saxiphilin).

In another embodiment, the method comprises: measuring the activity of gene expression of a fat regulating cathepsin of an animal; and measuring the blood sugar and/or insulin levels of the animal, wherein abnormally high activity of fat regulating cathepsin gene expression and abnormally high blood sugar and/or insulin levels indicate that the animal is genetically predisposed of hyperinsulinmia or type II diabetes.

In another embodiment, the method comprises: measuring the activity of gene expression of a fat regulating cathepsin of an animal; and measuring the blood sugar and/or insulin levels of the animal, wherein abnormally high activity of fat regulating cathepsin gene expression and abnormally high blood sugar and/or insulin levels indicate that the animal is genetically predisposed of hyperinsulinmia or type II diabetes.

By using the methods of diagnosis of the present invention, the molecular genetic pathogenesis of obesity and diabetes can be revealed by correlating the activity of a specific form of cathepsin with body fat content and/or blood sugar and insulin levels. In particular, this approach may be utilized to predict the onset of these diseases before the manifestation of the symptoms.

For example, the method can be used to diagnose insulin resistance in individuals. It has been found that insulin resistance is a sufficient cause of type II diabetes and in the majority of cases is necessary for development of this disease. Individuals with type II diabetes, or maturity onset diabetes mellitus, have higher plasma insulin concentrations that non-diabetics. These people are characterized by (1) obesity, particularly central obesity; (2) insulin resistance; (3) abnormal insulin secretory function; and (4) increased rates of post-absorptive hepatic glucose production. Thus, higher levels of blood insulin often correlate with higher blood glucose levels which are the conventional indicators of diabetes.

The diagnostic methods may, for example, utilize reagents such as the fingerprint gene nucleotide sequences for one or more fat regulating cathepsins (preferably including cathepsin L) and antibodies directed against differentially expressed cathepsin gene products. Specifically, such reagents may be used, for example, for: (1) the detection of the presence of cathepsin gene mutations, or the detection of either over- or under-expression of fat regulating cathepsin gene mRNA relative to the non-obese state; and (2) the detection of either an over- or an under-abundance of fat regulating cathepsin gene product relative to the non-obese state.

The methods described herein may be performed, for example, by utilizing pre-packaged diagnostic kits comprising at least one specific cathepsin gene nucleic acid or anti-cathepsin antibody reagent described herein, which may be conveniently used, e.g., in clinical settings, to diagnose patients exhibiting symptoms of obesity and related diseases.

Among the methods which can be utilized herein are methods for monitoring the efficacy of fat regulating cathepsin inhibitors in clinical trails for the treatment obesity and related diseases. The fat regulating cathepsin inhibitors that may be used include, but are not limited to those described above, in Section 3.

During clinical trials, for example, the expression of cathepsin L gene, or alternatively, a phenotype of a cell involved in expression of the gene, can be determined in the presence or absence of the inhibitor being tested. The efficacy of the inhibitor can be followed by comparing the expression data obtained to the corresponding known expression patterns in a normal, non-obese state. Agents exhibiting efficacy are those which reduce the cathepsin L gene expression and/or restore phenotype of cells to those more closely resemble that of the normal, non-obese state.

The detection of the product or products of cathepsin genes differentially expressed in an obese state relative to their expression in a normal, or non-obese state can also be used for monitoring the efficacy of potential cathepsin L inhibitors during clinical trials. During clinical trials, for example, the level and/or activity of the products of one or more such differentially expressed cathepsin genes can be determined in relevant cells and/or tissues in the presence or absence of the compound being tested. The efficacy of the compound can be followed by comparing the protein level and/or activity data obtained to the corresponding known levels/activities for the cells and/or tissues in a normal, non-obese state. Compounds exhibiting efficacy are those which alter the pattern of the cell and/or tissue involved in obesity to more closely resemble that of the normal, non-obese state.

EXAMPLES

Biochemical and cell biological studies are described to demonstrate that certain cathepsins, especially cathepsin L, play significant roles in regulating adipogenesis and the turnover of insulin-insulin receptor. Examples of methods used to inhibit cathepsin L activity are also described.

1. Materials and Methods a) Materials

All chemicals were purchased from Sigma and Aldrich (St. Lois, Mo.) except otherwise indicated. Rabbit anti-human/mouse cathepsins S, K, and L polyclonal antibodies, goat anti-human/mouse IR, IGF-1R, and C/EBP-α polyclonal antibodies, and mouse anti-human/mouse PPAR-γ monoclonol antibodies were all purchased from Santa Cruz Biotechnologies, Inc. (Santa Cruz, Calif.). CA 074 was from Bachem Biosciences Inc. (King of Prussia, Pa.). E64d was purchased from Calbiochem (San Diego, Calif.). Z-Tyr-Ala-CHN$_2$ was from the Enzyme Systems (Livermore, Calif.). CLIK 148 (L-(+)-(2S, 3S)-N-[2-(2'-pyridinyl)-1-ethyl]-Na-amino-(L-phenylalanine dimethylamide)-trans-epoxysuccinamide, IUPAC name: N-[2-(2-pyridinyl)-1-ethyl]-L-(+)-(2S,3S)-3-[(S)-1-dimethylcarbamoyl-2-phenylethylcarbamoyl)-2-oxiranecarboxamide), CLIK 060 (N-{L-3-trans[(1-phenylcarbamoyl-5-amino)pentylcarbamoyl]oxirane-2-carbonyl}-L-phenylalaninoldimethylamide hydrochloride), and CLIK 195 (L-(+)-(2S, 3S)-Bis-(Na-amino-L-phenylalaninedimethylamide)-trans-epoxysuccinamide, IUPAC name: N,N-Dimethyl-L-(+)-(2S,3S)-2-{3-[(S)-1-dimethylcarbamoyl-2-phenyl-ethylcarbamoyl]-2-oxirane carbomylamino}-(S)-3-phenyl-propionamide) were synthesized according to Katunuma et al. (1999) FEBS Lett. 458:6–10.

b) Human Preadipocyte Adipogenesis

Human preadipocytes were initially cultured in MSCGM medium (BioWhitaker) at 37° C. and 5% CO$_2$ for 7 to 12 days with 3–4 changes of media till complete confluence. Non-induced cells were kept in adipogenesis maintenance media containing 0.01 mg/ml of insulin, 0.05 units/ml of penicillin, 0.05 μg/ml of streptomycin, and 10% fetal bovine serum. To induce adipogenesis, complete confluent cells were cultured in adipogenesis induction medium containing 1 μM dexamethasone, 0.2 mM indomethacin, 0.01 mg/ml insulin, 0.5 mM 3-isobutyl-1-methyl-xanthine, 0.05 units/ml of penicillin, 0.05 μg/ml of streptomycin, and 10% fetal bovine serum in the presence and absence of protease inhibitors for 3 days followed by three days of culture in maintenance media. After three cycles of induction and maintenance, cells were cultured in maintenance media for additional 7 days with two changes of fresh media.

c) Mouse Preadipocyte Adipogenesis

Mouse preadipocytes were differentiated as described in Patel and Lane (2000) J. Biol. Chem. 275:17653–17660. In brief, mouse 3T3-L1 cells were cultured in DMEM containing 10% calf serum till confluence at 37° C. with 10% CO$_2$. After additional two days maintenance in the same media, cells were differentiated by adding 0.5 mM methylisobutylxanthine, 1 μM dexmethasone, 1 μg/ml insulin, and 10% FBS for two days in the presence and absence of protease inhibitors. Culture media were replaced with DMEM containing 1 μg/ml insulin and 10% FBS. After day 4 the cells were fed every other day with 10% FBS in DMEM without insulin. By days 7–8, cells were fully differentiated.

d) Western Blot Analysis

After differentiation, cells were collected, and lysed into 1×RIPA buffer. Protein concentrations were determined using Bio-Rad Dc protein assay system according to the manufacturer (Bio-Rad, Hercules, Calif.). Equal amount of proteins were separated on 7% SDS-PAGE for detecting IR and IGF-1R, 12% SDS-PAGE for detecting cathepsins S, K, and L antigens. Both IR and IGF-1R primary polyclonal antibodies were raised from goat and all cathepsin antibodies were polyclonal antibodies raised from rabbit. The corresponding HRP-conjugated secondary antibodies were used for detections.

e) Cysteine Protease Active Site Labeling

Mouse peritoneal macrophages were generated by injecting mice with thioglycolate as described in Shi et al. (2000) J. Exp. Med. 191:1177–1786. After 3–4 days of incubation, peritoneal microphages were washed out using Tris-EDTA buffers containing 6 mM EDTA (pH 8.0). Cells were then seeded onto 24-well plates in DMEM with 10% FBS till complete spread. After cells were attached to the plates, different doses of inhibitors were added. After 2–3 hours of incubation, cells were labeled with [$^{125}$I]-Z-Tyr-Ala-CHN$_2$ overnight at 37° C. to detect intracellular active cysteine proteases. Cells were lysed into 1× reducing protein sample buffer and separated onto 12% SDS-PAGE.

2. Results and Discussion

Cathepsins B, S, K, and L are lysosomal cysteine proteases that play very important roles in human pathophysiology. Cathepsin B is a house keeping type protease and its primary role is to degrade unwanted or recycled proteins translocated into acidic compartments endosomes and lysosomes. It is highly expressed in solid tumors and thus has been implicated in tumor invading and metastasis. Yan et al. (1998) Biol. Chem. 379:113–123. Cathepsin S, in contrast, is selectively expressed in antigen presenting cells and plays a role in invariant chain degradation and thus is required for MHC class II mediated immunity. Inhibition or deficiency of this protease resulted in impaired MHC class II processing and thus antigen presentation Shi et al. (1999) Immunity 10: 197–206; and Riese et al. (1996) Immunity 4:357–366. In addition, this protease has also been implicated in the pathogenesis of atherosclerosis as well as Alzheimer's disease. Sukhova et al. (1998) J. Clin. Invest. 102:576–583; and Munger et al. (1995) Biochem. J. 311:299–305. Cathepsin K is also a potent elastase, but primarily expressed in osteoclasts and thus is involved in bone metabolism. Gelb et al. (1996) Science 273:1236–1238; and Saftig et al. (1998) Proc. Natl. Acad. Sci. USA 95:13453–13458. Cathepsin L, another potent elastase just like cathepsins S and K, has been isolated for more than a decade ago. Gal and Gottesman (1988) Biochem. J. 253:303–306; and Joseph et al. (1988) J. Clin. Invest. 81:1621–1629. This protease is rather widely expressed. Its potent elastase activity made this protease one of the candidate enzymes for lung matrix breakdown in patients with emphysema. Reilly et al. (1991) Am. J. Physiol. 261:L41-L48. Recently, this protease has been implicated in thymic CD4$^+$ T cell selection. Nakagawa et al. (1998) Science 280:450–453.

The principle role of insulin is to control plasma glucose concentration by stimulating glucose transport into muscle and adipose cells, as well as by reducing glucose output from the liver. Birmbaum (1993) Int. Rev. Cytol. 137:239–297. Insulin signaling is mediated by its binding to cell surface receptor followed with autophosphoration and endocytosis via clathrin-coated vessicles (Backer et al. (1991) J. Cell Biol. 115:1535–1545), similar to other cell surface receptors (Tackyo et al (1983) J. Cell Biol. 97:1762-1776). Such complexes are finally degraded in acidic endosomes and/or lysosomes. However, the proteases responsible for this biological processing have been poorly understood. It has been suggested that cathepsin B degrades synthetic insulin peptide in vitro. Conlon et al. (1995) Peptide 16:1385–1388.

According to the present invention, it is hypothesized that cysteine protease may well be involved in insulin/insulin receptor turnover. To test this hypothesis, synthetic small molecule compounds were utilized as inhibitors to selectively block activities of cathepsins S, B, K, and L.

First, the synthetic small molecule compounds were tested for their selectivity toward different forms of cathepsin. Mouse peritoneal macrophages were cultured in the presence of selective inhibitors and cysteine protease active site labeling probe [$^{125}$I]-Z-Tyr-Ala-CHN$_2$ (Sukhova et al., supra). As shown in FIG. 1, cathepsin B activity can be completely blocked by 2 $\mu$M of CA 074 whereas cathepsins S, K, and L activities remain intact. In contrast, other inhibitors used had no effect on cathepsin B activity. CLIK 060 significantly inhibited catepsin S activity at 2–10 $\mu$M of concentration although cathepsin L activity was also affected at some level. CLIK 148 and CLIK 195, in comparison, were more selective for cathepsin L. At 10 $\mu$M of concentration they completely inhibited cathepsin L activity but not cathepsin B or cathepsin S or cathepsin K (FIG. 1). Therefore, these inhibitors can be utilized to test if the aforementioned cathepsins play roles in the breakdown of insulin receptor (IR) or IR turnover.

To test which cathepsin is involved in the IR turnover, human preadipocytes (BioWhittaker, Walkersville, Md.) were induced to become adipocytes in the presence and absence of inhibitors. Differentiated adipocytes expressed more IR than controls as previously reported. Pederson et al. (2000) Biochem. Biophys. Res. Commun. 276:162–168. Cathepsin B inhibitor (CA 074, 10 $\mu$M) and catepsin S inhibitor (CLIK 060, 2 $\mu$M) had no effect on either IR turnover or differentiation (FIGS. 2). In contrast, E64d (20 $\mu$M), CLIK 148 and CLIK 195 (10 $\mu$M) treated cells had increased levels of both 95 kDa IR β subunit as well as its precursor. The same is true when the blot was tested with insulin like growth factor I receptor (IGF-IR) antibodies (FIG. 3).

To evaluate the cell differentiation levels affected by aforementioned inhibitors, the levels of transcription factors CCAAT/enhancer-binding protein-α (C/EBP-α) as well as peroxisome proliferator-activated receptor-γ (PPAR-γ) from cells treated with and without inhibitors were measured. Both C/EBP-α and PPAR-γ are important adipocyte determination factors. Wu et al. (1999) Mol. Cell. 3:151–158; Tanaka et al. (1997) EMBO J. 16:7432–7443; and Tontonoz et al. (1994) Cell 79:1147–1156.

As shown in FIGS. 4 and 5, only E64d and CLIK 148 and CLIK 195 had the effect of blocking the accumulation of 50 kDa C/EBP-α (FIG. 4) and 50 kDa PPAR-γ (FIG. 5). These observations indicated that inhibition of cathepsin L may block human preadipocyte adipogenesis. This hypothesis is further confirmed by oil-red staining of CLIK 148 or 195 treated preadipocytes (FIG. 6). In addition, inhibition of adiogenesis by these two inhibitors is dose dependent. Less than 50% of adipogenesis was blocked by 1 $\mu$M of such inhibitors. A complete inhibition was observed if 10 $\mu$M of either CLIK 148 or CLIK 195 was used (FIG. 6). In contrast, 1 $\mu$M of CLIK 060, 1 or 10 $\mu$M of CA 074 had no effect on adipogenesis (data not shown). Therefore, these observations indicate that cathepsin L appears to play a more critical role than cathepsins S and K in adipogenesis by controlling insulin/IR complex turnover. Meanwhile, cathepsin B does not appear to play a critical role in this process.

Several lines of evidence support this observation. First, cathepsin B inhibitor CA 074 had no effect on adipogenesis even at higher concentrations (10–20 $\mu$M) (data not shown). Cathepsin S inhibitor CLIK 060 also had no effect at 1 $\mu$M, but had some effect at higher concentrations. Both IR accumulation and adipogenesis inhibition were observed when cells were treated with 10–15 $\mu$M of CLIK 060. It is noted that CLIK060 at these concentrations also blocked catepsin L activity (FIG. 1). In addition, western blot analysis of both differentiated cells and their controls showed that cathepsin L activity increased after the differentiation whereas cathepsin S activity disappeared in adipocytes as compared with non-differentiated cells (FIG. 7). Cathepsin K may be another potential player although cathepsin K signal in either preadipocytes or adipocytes were not detected, and all of the inhibitors used had no inhibitory effects on cathepsin K at the concentrations used (FIG. 1). Therefore, cathepsin L appears to be the most significant protein regarding controlling adipogenesis.

Similar phenotypes were observed using mouse preadipocytes 3T3-L1 (ATCC, Manassas, Va.). Both active cathepsins L and S were found in differentiated adipocytes (FIG. 8, days 8–11). However, levels of both enzyme increased after the differentiation, a phenomenon different from that of human preadipoicytes. In 3T3-L1 cells, the role for cathepsin L in adipogenesis was further confirmed by inhibition of adipogenesis with CLIK 148 (15 µM) (FIG. 9). The adipogenesis inhibition profile in this test suggested that the first 4 days of adipogenesis induction may be more important than the late days (days 5 to 9). Cathepsin K antigen was detected in preadipocytes but not adipocytes nor insulin treated cells (FIG. 10).

These results further confirm that cathepsin L appears to play a more critical role in adipogenesis than cathepsins S and K. Meanwhile, cathepsin B again does not appear to play a critical role. Selective reduction in the in vivo activity of cathepsins K, L and S, particularly cathepsin L, is therefore believed to be useful for treating obesity, diabetes and related diseases.

It will be apparent to those skilled in the art that various modifications and variations can be made in the compositions, kits, and methods of the present invention without departing from the spirit or scope of the invention. Thus, it is intended that the present invention cover the modifications and variations of this invention provided they come within the scope of the appended claims and their equivalents. Additionally, the above examples are provided for the purpose of illustrating the claimed invention, and should not be construed so as to limit the scope of the claimed invention.

TABLE 1

Full Length Human cathepsin L sequence

```
   1 agaaccgcga cctccgcaac cttgagcggc atccgtggag tgcgcctgca gctacgaccg   [SEQ ID NO:1]
  61 cagcaggaaa gcgccgccgg ccaggcccag ctgtggccgg acagggactg gaagagagga
 121 cgcggtcgag taggtgtgca ccagccctgg caacgagagc gtctaccccg aactctgctg
 181 gccttgaggt ggggaagccg gggagggcag ttgaggaccc cgcggaggcg cgtgactggt
 241 tgagcgggca ggccagcctc cgagccgggt ggacacaggt tttaaaacat gaatcctaca
 301 ctcatccttg ctgcctttg cctgggaatt gcctcagcta ctctaacatt tgatcacagt
 361 ttagaggcac agtggaccaa gtggaaggcg atgcacaaca gattatacgg catgaatgaa
 421 gaaggatgga ggagagcagt gtgggagaag aacatgaaga tgattgaact gcacaatcag
 481 gaatacaggg aagggaaaca cagcttcaca atggccatga acgcctttgg agacatgacc
 541 agtgaagaat tcaggcaggt gatgaatggc tttcaaaacc gtaagcccag gaaggggaaa
 601 gtgttccagg aacctctgtt ttatgaggcc cccagatctg tggattggag agagaaaggc
 661 tacgtgactc ctgtgaagaa tcagggtcag tgtggttctt gttgggcttt tagtgctact
 721 ggtgctcttg aaggacagat gttccggaaa actgggaggc ttatctcact gagtgagcag
 781 aatctggtag actgctctgg gcctcaaggc aatgaaggct gcaatggtgg cctaatggat
 841 tatgctttcc agtatgttca ggataatgga ggcctggact ctgaggaatc ctatccatat
 901 gaggcaacag aagaatcctg taagtacaat cccaagtatt ctgttgctaa tgacaccggc
 961 tttgtggaca tccctaagca ggagaaggcc ctgatgaagg cagttgcaac tgtgggggcc
1021 atttctgttg ctattgatgc aggtcatgag tccttcctgt tctataaaga aggcatttat
1081 tttgagccag actgtagcag tgaagacatg gatcatggtg tgctggtggt tggctacgga
1141 tttgaaagca cagaatcaga taacaataaa tattggctgg tgaagaacag ctggggtgaa
1201 gaatgggggca tgggtggcta cgtaaagatg gccaaagacc ggagaaacca ttgtggaatt
1261 gcctcagcag ccagctaccc cactgtgtga gctggtggac ggtgatgagg aaggacttga
1321 ctgggggatgg cgcatgcatg ggaggaattc atcttcagtc taccagcccc cgctgtgtcg
1381 gatacacact cgaatcattg aagatccgag tgtgatttga attctgtgat attttcacac
1441 tggtaaatgt tacctctatt ttaattactg ctataaatag gtttatatta ttgattcact
1501 tactgacttt gcattttcgt ttttaaaagg atgtataaat ttttacctgt ttaaataaaa
1561 tttaatttca aatgt
```

Human cathepsin L full length amino acids:

```
MNPTLILAAFCLGIASATLTFDHSLEAQWTKWKAMHNRLYGMNEEGWRRAVW   [SEQ ID NO:2]
EKNMKMIELHNQEYREGKHSFTMAMNAFGDMTSEEFRQVMNGFQNRKPRKGK
VFQEPLFYEAPRSVDWREKGYVTPVKNQGQCGSCWAFSATGALEGQMFRKTGR
LISLSEQNLVDCSGPQGNEGCNGGLMDYAFQYVQDNGGLDSEESYPYEATEESC
KYNPKYSVANDTGFVDIPKQEKALMKAVATVGPISVAIDAGHESFLFYKEGIYFE
PDCSSEDMDHGVLVVGYGFESTESDNNKYWLVKNSWGEEWGMGGYVKMAKD
RRNHCGIASAASYPTV-stop
```

Mouse cathepsin L full length cDNA:

```
  1 cggcgacctc cggggatccg agtttgcaga cttcttgtgc gcacgtagcc gcctcaggtg   [SEQ ID NO:3]
 61 tttgaaccat gaatctttta ctccttttgg ctgtcctctg cttgggaaca gccttagcta
121 ctccaaaatt tgatcaaacc tttagtgcag agtggcacca gtgaagtcc acgcacagaa
181 gactgtatgg cacgaatgag gaagagtgga ggagagcgat atgggagaag aacatgagaa
241 tgatccagct acacaacggg gaatacagca acgggcagca cggcttttcc atggagatga
301 acgcctttgg tgacatgacc aatgaggaat tcaggcaggt ggtgaatggc tatcgccacc
361 agaagcacaa gaagggggag cttttttcagg aaccgctgat gcttaagatc cccaagtctg
421 tggactggag agaaaagggt tgtgtgactc ctgtgaagaa ccagggccag tgcgggtctt
```

TABLE 1-continued

```
 481 gttgggcgtt tagcgcatcg ggttgcctag aaggacagat gttccttaag accggcaaac
 541 tgatctcact gagtgaacag aaccttgtgg actgttctca cgctcaaggc aatcagggct
 601 gtaacggagg cctgatggat tttgcttttcc agtacattaa ggaaaatgga ggtctggact
 661 cggaggagtc ttaccccctat gaagcaaagg acggatcttg taaatacaga gccgagttcg
 721 ctgtggctaa tgacacaggg ttcgtggata ccctcagca agagaaagcc ctcatgaagg
 781 ctgtggcgac tgtggggcct atttctgttg ctatggacgc aagccatccg tctctccagt
 841 tctatagttc aggcatctac tatgaaccca actgtagca caagaacctc gaccatgggg
 901 ttctgttggt gggctatggc tatgaaggaa cagattcaaa taagaataaa tattggcttg
 961 tcaagaacag ctggggaagt gaatggggta tggaaggcta catcaaaata gccaaagacc
1021 gggacaacca ctgtggactt gccaccgcgg ccagctatcc tgtcgtgaat tgatgggtag
1081 cggtaatgag gacttatgga cactatgtcc aaaggaattc agcttaaaac tgaccaaacc
1141 cttattgagt caaaccatgg tacttgaatc attgaggatc caagtcatga tttgaattct
1201 gttcccattt ttacatgggt taaatgttac cactacttaa aactcctgtt ataaacagct
1261 ttataatatt gaaaacttag tgcttaattc tgagtctgga atatttgttt tatataaagg
1321 ttgtataaaa ctttctttac ctcttaaaaa taaattttag ctcagtgtgt gtgt
```

Mouse cathepsin L full length amino acid seq:

MNLLLLLAVLCLGTALATPKFDQTFSAEWHQWKSTHRRLYGTNEEEWRRAIWE [SEQ ID NO:4]
KNMRMIQLHNGEYSNGQHGFSMEMNAFGDMTNEEFRQVVNGYRHQKHKKGR
LFQEPLMLKIPKSVDWREKGCVTPVKNQGQCGSCWAFSASGCLEGQMFLKTGK
LISLSEQNLVDCSHAQGNQGCNGGLMDFAFQYIKENGGLDSEESYPYEAKDGSC
KYRAEFAVANDTGFVDIPQQEKALMKAVATVGPISVAMDASHPSLQFYSSGIYY
EPNCSSKNLDHGVLLVGYGYEGTDSNKNKYWLVKNSWGSEWGMEGYIKIAKD
RDNHCGLATAASYPVVN-stop Human cathepsin L 5'-end UTR:

```
   1 agaaccgcga cctccgcaac cttgagcggc atccgtggag tgcgcctgca gctacgaccg [SEQ ID NO:5]
  61 cagcaggaaa gcgccgccgg ccaggcccag ctgtggccgg acagggactg aagagagga
 121 cgcggtcgag taggtgtgca ccagccctgg caacgagagc gtctacccccg aactctgctg
 181 gccttgaggt ggggaagccg gaagggcag ttgagggacc cgcgggaggc cgtgactggt
 241 tgagcgggca ggccagcctc cgagccgggt ggacacaggt accgcagcca ggccggcgcc
 301 aacgactcag ggcctggccc ggccagacag ggaagctcag tccccgcacg ccagacagcg
 361 gtactcctgc tggcgtcacc gcaaacatcc tctgaccgct acagccagtg tgtgggcagg
 421 cgtcatgtcc ccggccctgc cacgcctgga gccctggcag ggccctggct ggctctggct
 481 tccccgcgtgc gcccatatga ccccgtcccct gatttagggg agcagtttgg ggtgtcggca
 541 gcacaggccc aagtgaatga aggagggaag cagtgcgtgc tctccttccc agttttttcct
 601 gggaaagcat tcagaaagg tttcatttaa gagaggttg gggcggccag gtggctcact
 661 cctgtaatcc cagcactttg ggaggctgag gtgggcggat cacctgaggt cagtagttca
 721 gaccagcctg gccaacatgg tgaaaccccg tctctactga aaatacaaaa ttagacgggc
 781 gaggcggcgc acgcctgtag ttccagctat tcaagaggct gaggaagaat ggcttgaacc
 841 cgggaggcag aggttgctgt gagtcgatat cgcgccgttg aactccagcc tgggccacag
 901 agcaagactc catctcaaaa aataaataaa taaataaata aataaataaa taggagagat
 961 tggaaaactt atctcagctt ttggtgtttg ttagtcagga agatgtgtga aggcctccta
1021 actcttgggg atctctttgt ccctacttg ggaatcccac cttatcatta gtgaggtttt
1081 gcctgggcac gaaacctgga tttttgcga ttggtacaaa acctggatca accgtttccc
1141 ggtttcctag ttgttgcctt aagcttctca cacacaaggt agtttcatac ggttctcata
1201 acctaaattg tcatcgcata aactgtttca gctcctacag ctctggacag gctgcttttc
1261 atttttggtaa gtccatccag tacctccacg tgccctgttt ttctccaggc acatccttgg
1321 cctcttccac agtccttggg taaatgcttg ggagaataat ttaaatattt ttattctacc
1381 atggtggccc taattttcca gggggcagta agatggcttt ttaggattgg tctaatcaga
1441 tcctcatttt tgttcccttc ctaggtttta aaacatgaat ccta
```

Mouse cathepsin L 5'-end promoter region:

```
   1 gtacggctga ggtggaaatt ccacagcagg tctttttttt ctacgctttt cttacagaac [SEQ ID NO:6]
  61 caaggcacca cgctggcgtg aaccctccaa agtggatcag cctcgcccca aggcttgcac
 121 cacaggacag gttacgaccc ggcggcgtc acgcgcccgg actcccgcag gctccgcccc
 181 gaggcaggca tagccaatga gggcggggg gcgggccctg tcggggctgt agcctgagag
 241 cctttaaagc ctgagcccgg cgctgctcct ccagattctc ggacctcggc gacctccggg
 301 gatccgagtt tgcagacttc ttgtgcgcag ctagccgcct caggtgagtg acccccgcgg
 361 gtttaaaggc ttcccgagca agggcaggta ggggaatcta gaatgtggga accatagcat
 421 ctgcaacccg gactggagac ccccggatgg gccaggatct cgaggatgtg tcctcggcct
 481 ccccgaagtg ataggcccctt gttgtcgagc gggtcttca tcaggtcatg tgactccggg
 541 ctgccgggac ccgtagggac agcgggaccc cctcaagctg gtcacgggac ccagggctcc
 601 ttatgccgcc ataacattcg cggcggtgg cccgagcgcg gagcggacgc catcccccct
 661 ctccccccgga cgggcccagc ttggccccta acccgaactg agatcgcata aggaggcatc
 721 gccttgaggc ttcagttcgc ctgatgtgca gctgtcgtt aaagtgtgtg gtggcagccc
 781 accctctggg tattcctgta tgcccacttg gggtcactaa tacttgtcaa taaatgacct
 841 ggacccagtt gtcctcttaa gattttgacg catacatatt cggaagactt aagactaccg
 901 tggccctata ataagagaaa ggtggggagg gggggctgt cgagatggtt cagcgggtaa
 961 gagcactgac cgttctttca aaggtcctga gtgcaaatct cagcaaccac atggtggctc
1021 acaaccaccc ataatgagat ctgacacccct cttcagtgc gtcaaaaatc agctacagtg
1081 tacttatgta tgataataaa tcctaataaa taaaagagaa aagggtttat ccctgttcca
1141 atgactacta ggctgttttt gtttcagtag ctagagtcta gtaacctcca aagattaatt
1201 cctgacttgt ttttctccac tcataatcac atttgttaac acgtgcaagg atgcttcaac
```

TABLE 1-continued

```
1261 tcagaacggt ttactgctgg gctggtggct catggatccc taaacttgag agatgggtca
1321 ttgaaaaagt ttaaagcctg aactacatga gaaactgtcc ttaaaagaga aagcttccgt
1381 gggattctca tttcctcttt ttccttccct aggtgtttga ac
```

TABLE 2

Cathepsin S Selective Inhibitors

| Group of Inhibitors and Structures | Inhibitory Potency (Reference) |
| --- | --- |
| A. α-Keto-β-Aldehyde Derivatives | Cathepsin S: Ki = 0.185 nM<br>Cathepsin B: Ki = 0.76 nM<br>(Walker et al. Biochem. Biophys. Res. Comm. 275, 401–405, 2000). |
| B. Vinyl Sulfones | Cathepsin S: Ki = 5 nM<br>Cathepsin L: Ki = 1 μM<br>(Palmer et al. J. Med. Chem. 38, 3193–3196, 1995). |

TABLE 3

Cathepsin K Selective Inhibitors

| Group of Inhibitors and Structures | Inhibitory Potency (Reference) |
| --- | --- |
| A. Non-Peptide Cyanamides | Cathepsin K: $IC_{50}$ = 0.04 μM<br>Cathepsin L: $IC_{50}$ = 0.054 μM<br>Cathepsin B: $IC_{50}$ = 0.20 μM |
| | Cathepsin K: $IC_{50}$ = 0.005 μM<br>Cathepsin L: $IC_{50}$ = 0.006 μM<br>Cathepsin B: $IC_{50}$ = 0.15 μM<br>(Falgueyret et al. J. Med. Chem. 44, 94–104, 2001). |

TABLE 3-continued

Cathepsin K Selective Inhibitors

| Group of Inhibitors and Structures | Inhibitory Potency (Reference) |
| --- | --- |
| B. Non-Peptide Carbohydrazides | |
| *[structure]* | Cathepsin K:<br>$K_{obs}^{[1]} = 3{,}100{,}000\ M^{-1}S^{-1}$<br>$K_{iapp} = nM$<br>(Thompson et al. J. Med. Chem. 41, 3923–3927, 1998). |
| C. Alkoxymethylketone Derivatives | |
| *[structure]* | Cathepsin K: Ki = 22 nM<br>Cathepsin L: Ki = 63 nM<br>Cathepsin B: Ki = 1310 nM<br>(Marquis et al. Bioorg. Med. Chem. 7, 581–588, 1999). |

TABLE 4

Cathepsin L Selective Inhibitors

| Group of Inhibitors and Structures | Inhibitory Potency (Reference) |
| --- | --- |
| A. Polypeptides | |
| Mutant Cystatin C (V10W/W106W) | Cathepsin B: Ki > 500 nM<br>Cathepsin H: Ki > 500 nM<br>Cathepsin L: Ki = 0.0024 nM<br>Cathepsin S: Ki = 0.19 nM<br>(Mason et al. Biochem. J. 330, 833–838, 1998). |
| Saxiphilin | Papain: Ki = 1.72 nM<br>Cathepsin B: Ki = 1.67 nM<br>Cathepsin L: Ki = 0.02 nM<br>(Lenarcic et al. J. Biol. Chem. 274, 15572–15577, 2000). |
| B. Epoxysuccinate Derivatives | |
| *[structure]* | % of Inhibition at $1 \times 10^{-6}$ M<br>Cathepsin L: 100%<br>Cathepsin S: 30%<br>Cathepsins B, K, C: 0%<br>(Katunuma et al. FEBS Lett. 458, 6–10, 1999). |

TABLE 4-continued

Cathepsin L Selective Inhibitors

| Group of Inhibitors and Structures | Inhibitory Potency (Reference) |
|---|---|
| 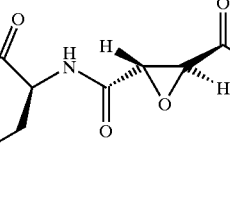 | % of Inhibition at $1 \times 10^{-6}$ M<br>Cathepsin L: 100%<br>Cathepsin S: 25%<br>Cathepsins B, K, C: 0%<br>(Katunuma et al. FEBS Lett. 458, 6–10, 1999). |
| C. Aziridine-2,3-Dicarbonate Derivatives | |
| 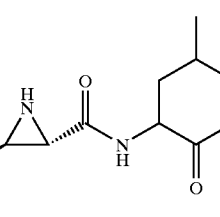 | Cathepsin L: $K_{2nd} = 16,261$ $M^{-1}Min^{-1}$<br>Cathepsin B: $K_{2nd} = 1,607$ $M^{-1}Min^{-1}$<br>Papain: $K_{2nd} = 1,533$ $M^{-1}Min^{-1}$<br>Schirmeister and Peric. Bioorg. Med. Chem. 8, 1281–1291, 2000). |
| 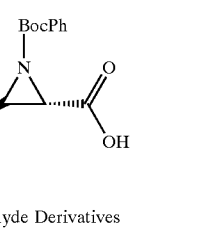 | Cathepsin B: $K_{2nd} = 38,081$ $M^{-1}Min^{-1}$<br>Cathepsin L: $K_{2nd} = 807$ $M^{-1}Min-1$<br>Papain: $K_{2nd} = 3,544$ $M^{-1}Min^{-1}$<br>(Schirmeister. J. Med. Chem 42, 560–572, 1999) |
| D. Peptide Aldehyde Derivatives | |
| 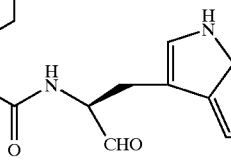 | Cathepsin L: $IC_{50} < 7$ nM<br>Cathepsin B: $IC_{50} > 100$ nM |
| 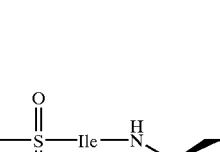 | Cathepsin L: $IC_{50} < 5$ nM<br>Cathepsin B: $IC_{50} > 1000$ nM |
| 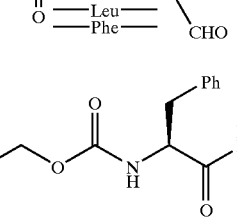 | Cathepsin L. Selective<br>(Woo et al. Bioorg. Med. Chem. 5, 1501, 1995) |

TABLE 4-continued

Cathepsin L Selective Inhibitors

| Group of Inhibitors and Structures | Inhibitory Potency (Reference) |
|---|---|
| 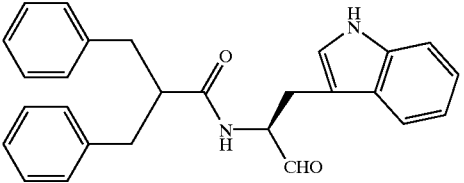 | Cathepsin L: $IC_{50} < 32$ nM<br>Cathepsin B: $IC_{50} > 1000$ nM<br>(Yasuma et al: J. Med. Chem. 41, 4301–4308, 1998). |
| E. Dipeptide Hydroxamates and Sulfonyl Derivatives | |
| 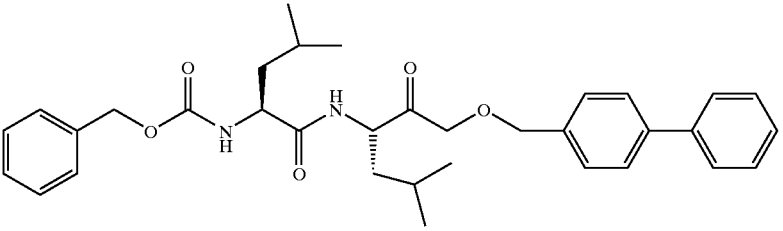 | Cathepsin L: Ki = 63 nM<br>Cathepsin B: Ki = 1310 nM<br>Cathepsin K: Ki = 22 nM<br>(Marquis et al. Bioorg. Med. Chem. 7, 581–588, 1984). |
| 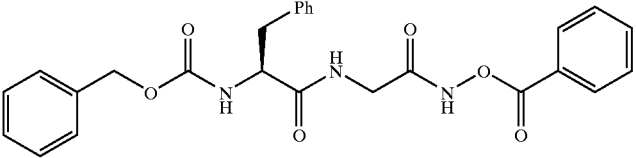 | Cathepsin L: Ki = 0.04–0.08 nM<br>Cathepsin B: Ki = 0.8–0.9 nM<br>Cathepsin K: Ki = 12–16 nM<br>Papain: Ki = 2–5 nM |
| 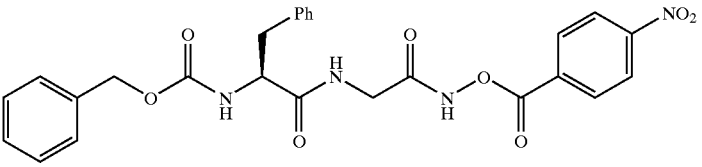 | (Demuth et al. Biochim. Biophys. Acta. 1295, 179–186, 1996) |
| 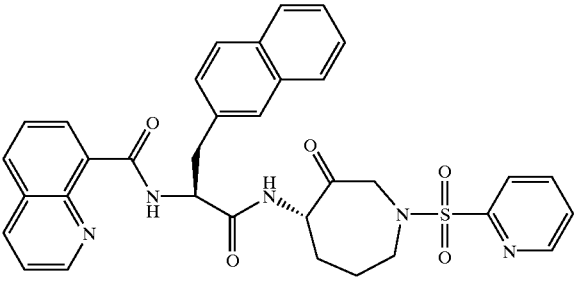 | Cathepsin L: Ki = 0.03–0.009 nM<br>Cathepsin K: Ki = 420–503 nM |
| 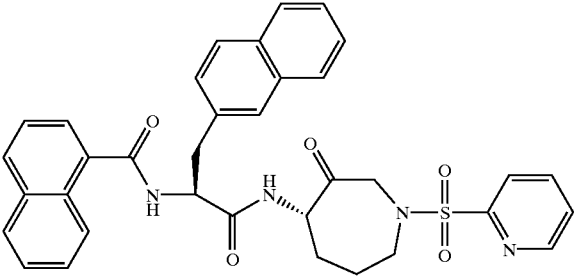 | Cathepsin L: Ki = 0.03–0.009 nM<br>Cathepsin K: Ki = 420–503 nM |

TABLE 4-continued

Cathepsin L Selective Inhibitors

| Group of Inhibitors and Structures | Inhibitory Potency (Reference) |
|---|---|
| [Structure: 1-naphthalenesulfonyl-Val-NH-Trp or Tyr or Phe] | Cathepsin L: $IC_{50}$ < 2 nM<br>Cathepsin B: $IC_{50}$ > 1300 nM<br>(Yasuma et al: J. Med. Chem. 41, 4301–4308, 1998). |

What is claimed is:

1. A method for treating hyperinsulinmia by reducing a blood insulin level of an animal comprising:

administering to the animal an agent which reduces an in vivo level of cathepsin L activity such that the blood insulin level of the animal is reduced.

2. The method according to claim 1, the method further comprising measuring the in vivo level of cathepsin L activity.

3. The method according to claim 2, the method further comprising determining an amount of the agent administered to the animal based on the measured cathepsin L activity.

4. The method according to claim 1, the method further comprising measuring a blood sugar level, an insulin level, body mass index and/or a fat content of the animal.

5. The method according to claim 4, the method further comprising determining an amount of the agent administered to the animal based on the measured blood sugar level, insulin level, body mass index and/or fat content of the animal.

6. The method according to claim 1, wherein reducing the in vivo level of cathepsin L activity comprises reducing a level of expression of cathepsin L by the animal.

7. The method according to claim 1, wherein reducing the in vivo level of cathepsin L activity comprises inhibiting cathepsin L expressed by the animal.

8. The method according to claim 1, wherein a reduction of the in vivo level of cathepsin L activity is evidenced by a change in a number of adipocytes of the animal.

9. The method according to claim 1, wherein a reduction of the in vivo level of cathepsin L activity is evidenced by a change in a level of insulin receptor of the animal.

10. The method according to claim 1, wherein a reduction of the in vivo level of cathepsin L activity is evidenced by a change in a level of expression of an CCAAT/enhancer-binding protein.

11. The method of claim 1, wherein the agent is an epoxysuccinate derivative that inhibits the activity of cathepsin L.

12. The method of claim 11, wherein the epoxysuccinate derivative has a chemical structure

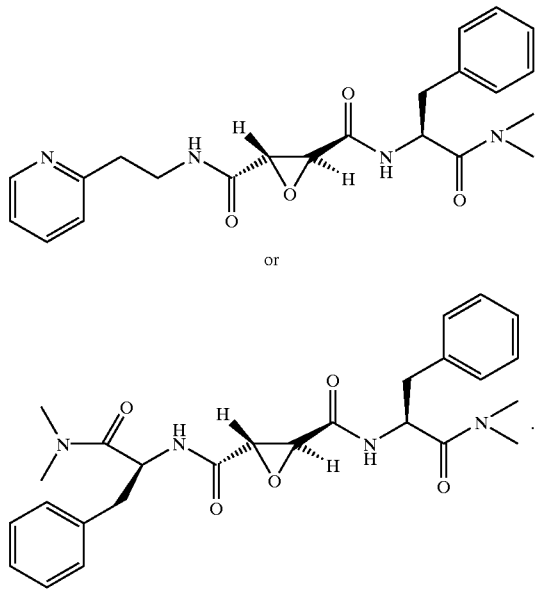

13. The method according to claim 1, wherein the agent more significantly reduces the in vivo activity of cathepsins L, K, or S than cathepsin B.

14. The method according to claim 1, wherein the agent more significantly reduces the in vivo activity of cathepsin L than cathepsins K or S.

15. The method according to claim 1, wherein the agent has at least 10 times greater binding affinity for cathepsin L than cathepsins K or S.

16. The method according to claim 1, wherein the agent has at least 100 times greater binding affinity for cathepsin L than cathepsins K or S.

17. The method according to claim 1, wherein the agent has at least 1000 times greater binding affinity for cathepsin L than cathepsins K or S.

18. The method according to claim 1, wherein the animal is selected from the group consisting of cats, dogs, horses, chickens, turkeys, ostriches, ducks, geese, cattle, pigs, sheep, and goats.

19. The method according to claim 1, wherein the animal is a form of livestock.

20. The method according to claim 1, wherein the animal is a human.

21. The method of claim 1, wherein the animal is a human having a blood sugar level higher than 1.26 grams of glucose per liter of blood.

22. The method of claim 21, wherein the human has type II diabetes.

* * * * *